United States Patent
Kim et al.

(10) Patent No.: US 10,864,162 B2
(45) Date of Patent: Dec. 15, 2020

(54) MASS PRODUCTION AND SIZE CONTROL OF NANOPARTICLES THROUGH CONTROLLED MICROVORTICES

(71) Applicants: Massachusetts Institute of Technology, Cambridge, MA (US); The Brigham and Women's Hospital, Inc., Boston, MA (US); Icahn School of Medicine at Mount Sinai, New York, NY (US); New York University, New York, NY (US)

(72) Inventors: YongTae Kim, Suwanee, GA (US); Zahi Fayad, Larchmont, NY (US); Willem J. Mulder, New York, NY (US); Edward Fisher, Scarsdale, NY (US); Francois Fay, New York, NY (US); Omid C. Farokhzad, Waban, MA (US); Robert Langer, Newton, MA (US)

(73) Assignees: MASSACHUSETTS INSTITUTE OF TECHNOLOGY, Cambridge, MA (US); THE BRIGHAM AND WOMEN'S HOSPITAL, INC., Cambridge, MA (US); ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 697 days.

(21) Appl. No.: 15/617,557

(22) Filed: Jun. 8, 2017

(65) Prior Publication Data
US 2017/0333348 A1 Nov. 23, 2017

Related U.S. Application Data

(62) Division of application No. 14/409,264, filed as application No. PCT/US2013/046581 on Jun. 19, 2013, now abandoned.

(Continued)

(51) Int. Cl.
*A61K 9/14* (2006.01)
*A61K 9/51* (2006.01)

(52) U.S. Cl.
CPC .............. *A61K 9/146* (2013.01); *A61K 9/145* (2013.01); *A61K 9/5153* (2013.01);
(Continued)

(58) Field of Classification Search
CPC ...... A61K 9/145; A61K 9/146; A61K 9/5153; A61K 9/5176; A61K 9/5192;
(Continued)

(56) References Cited

U.S. PATENT DOCUMENTS 7,052,678 B2   5/2006   Vanbever
8,057,839 B2  11/2011   Bovetto et al. ........... A23J 3/08
                                                          426/520

(Continued)

FOREIGN PATENT DOCUMENTS

JP      2006266974 A    10/2006
WO   WO 2007150030 A2   12/2007  .......... A61K 9/5153

OTHER PUBLICATIONS

Li, Hao et al. "Lack of ApoA-I is Not Associated With Increased Susceptibility to Atherosclerosis in Mice", Arterioscler Thromb. 1993; vol. 13; p. 1814-1821.—Reference submitted by Applicant in response filed on May 29, 2020 (Year: 1993).*

(Continued)

*Primary Examiner* — Lyle Alexander
*Assistant Examiner* — Bryan Kilpatrick
(74) *Attorney, Agent, or Firm* — Pabst Patent Group LLP

(57) ABSTRACT

Methods for making particles, such as nanoparticles, devices useful in the methods, and particles made by the method are described herein. The methods involves the use of microfluidic device, such that upon mixing solutions of the materials to form the particles (or a solution of the material (Continued)

or materials to form the particles and a non-solvent for the material or materials) at least two symmetrical microvortices are formed simultaneously. The method can be used to prepare polymeric or non-polymeric particles and hybrid particles, such as lipid-polymer hybrid particles, as well as such particles containing one or more agents associated with the particles.

37 Claims, 11 Drawing Sheets

Related U.S. Application Data

(60) Provisional application No. 61/661,662, filed on Jun. 19, 2012.

(52) U.S. Cl.
CPC .......... *A61K 9/5176* (2013.01); *A61K 9/5192* (2013.01); *Y10T 428/2982* (2015.01)

(58) Field of Classification Search
CPC .............. A61K 47/6929; A61K 9/5089; Y10T 428/2982; C12M 23/16
See application file for complete search history.

(56) References Cited

U.S. PATENT DOCUMENTS

| | | |
|---|---|---|
| 2005/0213425 A1 | 9/2005 | Wang |
| 2010/0022680 A1* | 1/2010 | Karnik .............. A61K 47/6937 523/105 |
| 2013/0014828 A1 | 1/2013 | Kim |

OTHER PUBLICATIONS

JPO, machine translation for "JP 2006266974 A", 2016, p. 1-6.
Bowen, "Particle size distribution measurement from millimeters to nanometers and from rods to platelets", J Dispersion Sci Tech., 23(5):631-62 (2002).
Chang, et al., "Nanoscale Electrokinetics and Microvortices: How Microhydrodynamics Affects Nanofluidic Ion Flux", Ann. Rev. Fluid Mech., 44;401-26 (2011).
Clawson, et al., "Synthesis and characterization of lipid-polymer hybrid nanoparticles with pH-triggered poly(ethylene glycol) shedding", Langmuir, 27(17):10556-61 (2011).
Fang, et al., "Quick synthesis of lipid-polymer hybrid nanoparticles with low polydispersity using a single-step sonication method", Langmuir, 26(22):16958-62 (2010).
Fang and Zhang, "Dispersion-based methods for the engineering and manufacture of polymeric nanoparticles for drug delivery applications", J Nanoeng Nanomanuf., 1:106-12 (2011).
Karnik, et al., "Microfluidic platform for controlled synthesis of polymeric nanoparticles", Nano Lett.,, 8(9):2906-12 (2008).
Kim, et al., "Mass production and size control of lipid-polymer hybrid nanoparticles through controlled microvortices", Nano Lett., 12(7):3587-91 (2012).
Kim, et al., "Dynamic control of 3D chemical profiles with a single 2D microfluidic platform", Lab Clip, 11(13):2182-8 (2011).
Kim, et al., "Three-dimensional chemical profile manipulation using two-dimensional autonomous microfluidic control", J Am Chem Soc., 132:1339-47 (2010).
Kolishetti, et al., "Engineering of self-assembled nanoparticle platform for precisely controlled combination drug therapy", PNAS, 107(42):17939-44 (2010).
Kozikowski, et al., "Synthesis of urea-based inhibitors as active site probes of glutamate carboxypeptidase II: efficacy as analgesic agents", J. Med. Chem., 47:1729-38 (2004).
Low, et al., "Folate receptor-targeted drugs for cancer and Inflammatory diseases", Adv. Drug Deliv. Rev., 56:1055-8 (2004).
Martins, et al., "Lipid-based colloidal carries for peptide and protein delivery-liposomes versus lipid nanoparticles", Int J Nanomedicine, 2(4):595-607 (2007).
Nan, et al., "Dual function glutamate-related ligands: discovery of a novel, potent inhibitor of glutamate carboxypeptidase II possessing mGluR3 agonist activity", J. Med. Chem., 43:772-4 (2000).
Rhee, et al., "Synthesis of size-tunable polymeric nanoparticles enabled by 3D hydrodynamic flow focusing in single-layer microchannels", Adv Mater., 23:H79-H83 (2011).
Stott, et al., "Isolation of circulating tumor cells using a microvortex-generating herringbone-chip", PNAS, 107(43):18392-97 (2010).
Shelby and Chiu, "Controlled rotation of biological micro- and nano-particles in microvortices", Lab Clip, 4(3)168-70 (2004).
Shelby, et al., "Microfluidic systems: high radial acceleration in microvortices", Nature, 425(6953):38 (2003).
Valencia, et al., "Single-step assembly of homogenous lipid-polumeric and lipid-quantum dot nanoparticles enabled by microfluidic rapid mixing", ACS Nano., 4(3):1671-9 (2010).
Yang, et al.,"A rapid micro-mixer/reactor based on arrays of spatially impinging micro-jets", J.Micromech Microengineering , 14(10):1345-51 (2004).
Zhang, et al., "Self-assembled lipid-polymer hybrid nanoparticles; a robust drug delivery platform", ACS Nano, 2(8):1695-702 (2008).

\* cited by examiner

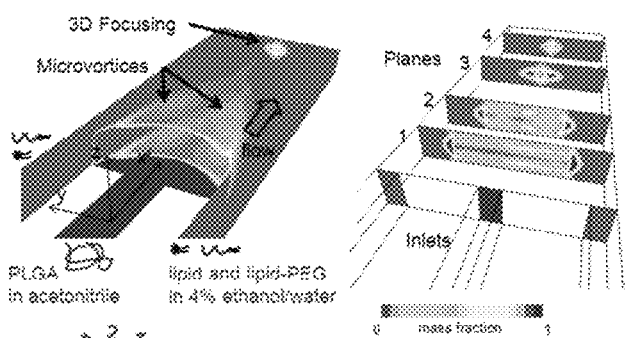
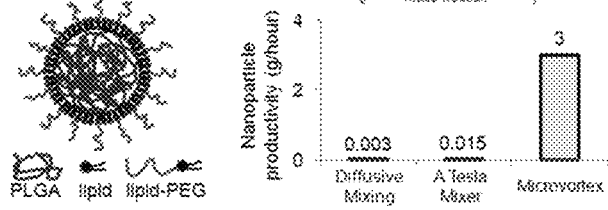
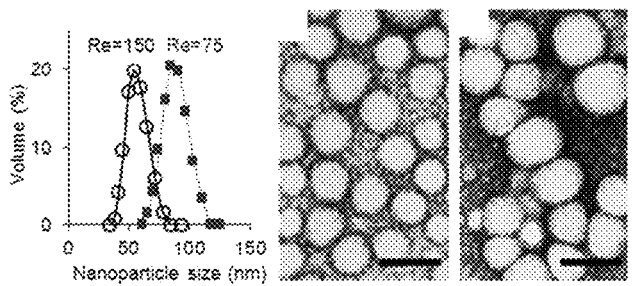
FIG. 1A  FIG. 1B  FIG. 1C  FIG. 1D  FIG. 1E  FIG. 1F  FIG. 1G

FIG. 4A
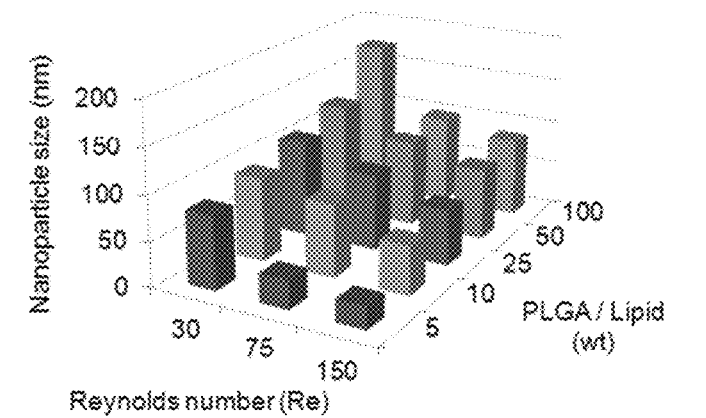
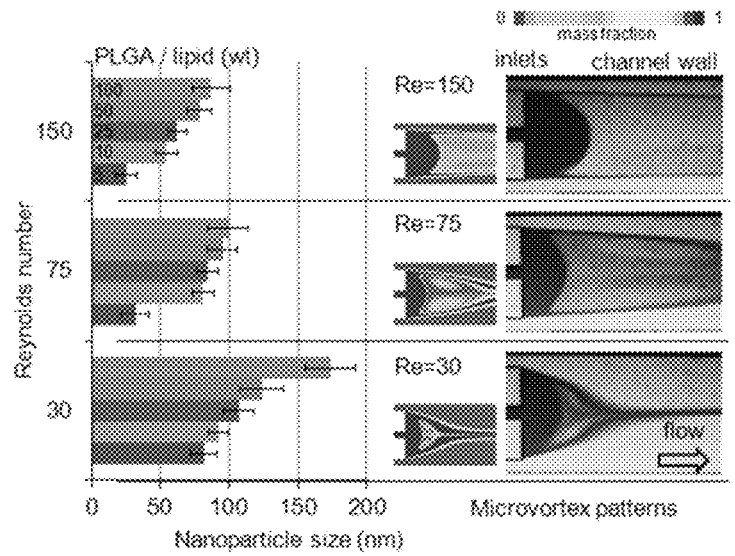
FIG. 4B      FIG. 4C

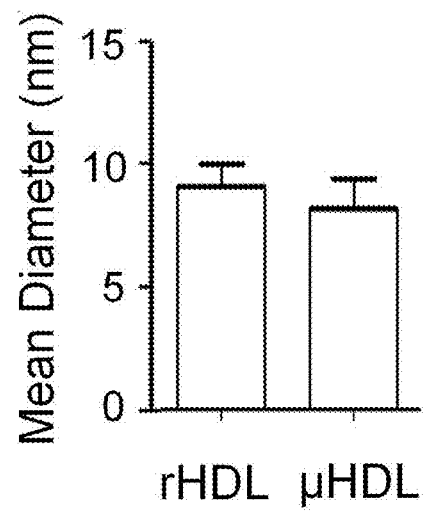
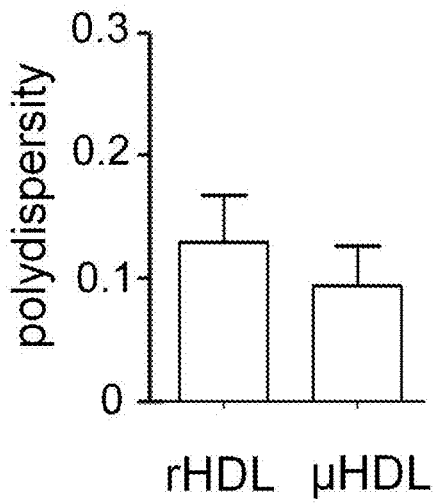
FIG. 12A  FIG. 12B
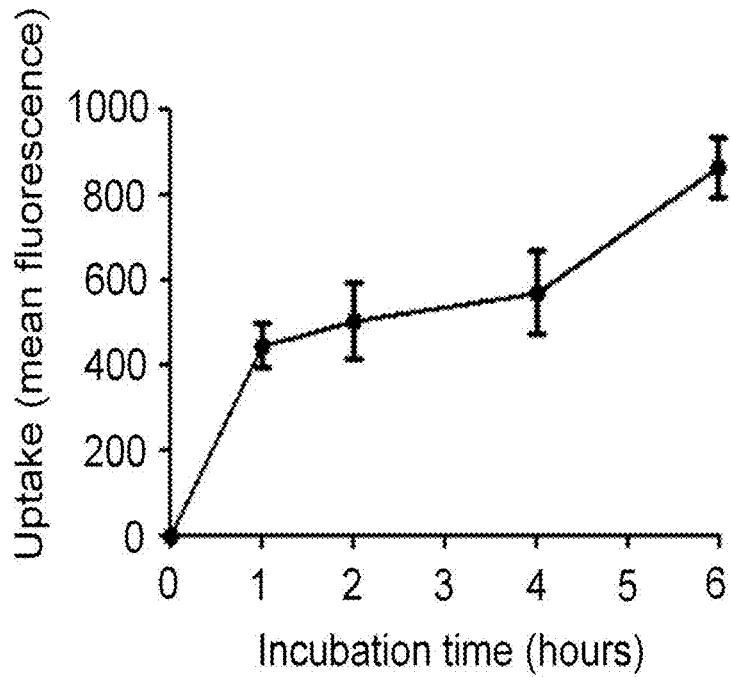
FIG. 13

MASS PRODUCTION AND SIZE CONTROL OF NANOPARTICLES THROUGH CONTROLLED MICROVORTICES

This application is a divisional of U.S. Ser. No. 14/409,264, filed Dec. 18, 2014, which is a 371 application of PCT/US2013/046581, filed Jun. 19, 2013, which claims priority to and benefit of U.S. Provisional Application No. 61/661,662, filed Jun. 19, 2012, the disclosures of which are hereby incorporated herein by reference in their entirety.

STATEMENT REGARDING FEDERALLY SPONSORED RESEARCH OR DEVELOPMENT

This invention was made with government support under Agreement HHSN268201000045C awarded by the National Institutes of Health. The government has certain rights in the invention.

FIELD OF THE INVENTION

This invention is in the field of methods for making particles, such as nanoparticles, devices for use therein, and particles made by the methods.

BACKGROUND OF THE INVENTION

Biodegradable, drug-encapsulated polymeric nanoparticles can be synthesized using established methods such as nanoprecipitation. Nanoprecipitation techniques vary nanoparticle design parameters to adjust the physicochemical features such as drug loading and nanoparticle stability, as well as biological features such as cellular specificity. However, conventional bulk techniques, which involve dropwise addition of polymers in an organic solution to a water-based solution, have faced critical challenges that include poor reproducibility, polydisperse size distribution, and batch-to-batch variations in nanoparticle physicochemical properties. These problems mainly result from the inability to control the mixing processes required for nanoparticle syntheses because bulk methods involve macroscopic mixing of precursor solutions although their microscale interactions determine nanoparticle formation and characteristics. Highly controlled microscale mixing processes that can produce targeted nanoparticles with optimal physicochemical properties are needed.

Continuously focused laminar flows in microfluidics (e.g. two-dimensional (2D) hydrodynamic focusing) have been used to synthesize a diversity of micro/nanoparticles 12-16. In these approaches, lateral diffusive dispersion across the interface of parallel streams flowing alongside in microfluidics induces relatively controlled mixing of nanoparticle precursors compared to conventional bulk methods. For example, an approach to controlled synthesis of PLGA-PEG polymeric nanoparticles, which has the ability to regulate single-step nanoprecipitation, was developed for nanoparticle-facilitated drug delivery. While these approaches have provided significant advantages, there still remain challenges. First, these microfluidic approaches using slow diffusive mixing at a low flow rate (i.e. Reynolds number (Re<1) (ratio of inertial to viscous forces) are basically limited to low productivity without complicated fabrication for high-throughput platforms. Second, diffusive mixing does not allow the development of particles that require the assembly of water soluble precursors with precursors in the organic phase such as lipid-polymer hybrid nanoparticles. Third, slow passive mixing requires longer storage of the polymers and their resulting exposure to organic solvent, which may cause unnecessary polymer aggregation and thereby lead to undesired variations in physicochemical properties.

To overcome these challenges and obtain a high-throughput and reproducible nanoparticle synthesis technology, rapid mixing of nanoparticle precursors is required and the mixing process needs to be highly controlled.

SUMMARY OF THE INVENTION

Methods for making particles, such as nanoparticles, devices useful in the methods, and particles made by the method are described herein. The method can be used to prepare polymeric or non-polymeric particles and hybrid particles, such as lipid-polymer hybrid particles, as well as such particles containing one or more agents associated with the particles.

The methods described herein involve creating three-dimensional (3D) combined-flow-interface patterns in multi-lane fluidic devices. The 3D-pattern can be varied as a function of one or more of the geometry of the inlets to a main fluidic channel in which the 3D-pattern is formed, the Reynolds number of the flows, the dimensions of the main fluidic channel and the inlets, and the spacing of adjacent inlets. In some embodiments, 3D combined-flow-interface patterns are created using a three-lane fluidic device having a fixed inlet geometry.

The method involves mixing a solution of one or more materials that form the particle with a second solvent or solution, which is a non-solvent for the one or more materials. Upon mixing, the at least two solutions/solvents form a three-dimensional pattern containing at least two symmetrical microvortices that form simultaneously. The particles are formed at the interface of the two solutions.

In some embodiments, the diameter of about 25% or less of the particles varies from the mean particle diameter by more than about 150%, 100%, 75%, 50%, 25%, 20%, 15%, 10%, or 5%. It is often desirable to produce a population of particles that is relatively uniform in terms of size, shape, and/or composition so that each particle has similar properties. For example, at least 80% 85%, 90%, 95%, 96%, 97%, 98%, or 99% of the particles produced using the methods described herein have a diameter that falls within 5%, 10%, 15%, or 20% of the average diameter. In other embodiments, a population of particles may be heterogeneous with respect to size, shape, and/or composition.

Zeta potential is a measurement of surface potential of a particle. In some embodiments, produced particles have a zeta potential ranging between −300 mV and +300 mV. In some embodiments, produced particles have a zeta potential ranging between −100 mV and +100 mV. In some embodiments, produced particles have a substantially neutral zeta potential (i.e. approximately 0 mV). In some embodiments, produced particles have a negative zeta potential. In some embodiments, produced particles have a positive zeta potential.

In some embodiments, particles produced using the methods are described herein are microparticles (e.g. microspheres). In general, a "microparticle" refers to any particle having a diameter of less than 1000 μm. In some embodiments, produced particles are nanoparticles (e.g. nanospheres). In general, a "nanoparticle" refers to any particle having a diameter of less than 1000 nm.

In some embodiments, the particles are prepared from one or more polymeric materials. The polymeric materials can be biocompatible. The polymeric materials can be biocompatible and biodegradable or non-biodegradable. In other embodiments, the particles are prepared from one or more lipids, such as phospholipids.

In the embodiments where the particles are prepared from one or more polymeric materials, the particles can be produced at a rate of at least about 0.025, 0.05, 0.1, 0.15, 0.2, 0.25, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, or 4.0 grams of particles per hour of fluid flow. The average size of the particles can be varied by varying a number of parameters, such as Reynolds number. In some embodiments, the average size is from about 5 nm to about 200 nm, preferably about 5 nm to about 150 nm, more preferably from about 5 nm to about 50 nm. In some embodiments, the polydispersity is less than about 0.1.

In the embodiments where the particles are prepared from one or more lipids, the particles can be prepared at a rate of at least 100, 125, 150, 165, 200, 225, 250, 275, 300, 325, 350, 375, 400, or 420 mg/hr. The average size of the particles can be varied by varying a number of parameters, such as Reynolds number. In some embodiments, the average size is from about 5 nm to about 50 nm, preferably about 5 nm to about 40 nm, more preferably from about 5 nm to about 30 nm, most preferably from about 8 nm to about 30 nm. In some embodiments, the polydispersity is less than about 0.1, such as from about 0.094 to about 0.102.

BRIEF DESCRIPTION OF THE DRAWINGS

FIG. 1a is a schematic of a single-layer, three-inlet microfluidic platform generating two symmetric microvortices and a 3D focusing pattern. FIG. 1b is a cross sectional view of a single-layer, three-inlet microfluidic platform generating two symmetric microvortices and a 3D focusing pattern. FIG. 1c is an illustrative structure of LPH nanoparticles synthesized in the microfluidic platform. FIG. 1d is a graph showing that productivity of PLGA-PEG particle synthesis as a function of the method of synthesis. FIG. 1e is a graph showing the average distribution of the nanoparticles produced through the controlled microvortices. The average sizes are 55 nm (Re=150) and 81 nm (Re=75). The Reynolds number was computed by the microfluidic dimensions and flow rate used in the experiment. FIGS. 1f and g are transmission electron microscopy (TEM) images that demonstrate the synthesized nanoparticles with two distinct sizes for Re=150 (f) and Re=75 (g) with only changes of flow rates (i.e. Reynolds number (Re)). The scale bars are both 100 nm.

FIG. 4a is a nanoparticle size map created by varying Reynolds number with given polymer-to-lipid weight ratios. The size represents the average value in the monodisperse distribution that occupies more than 85% of the overall volume of the produced nanoparticles. FIG. 4b is a graph showing nanoparticle size manipulated by controlled microvortex patterns that vary the polymer-lipid mixing times. The error bars are standard deviations of different nanoparticle batches. FIG. 4c are microvortex patterns predicted by the computational fluid dynamics simulations and visualized by microscopic images. Simulated and predicted desired flow patterns were determined using computational fluid dynamics (CFD), which demonstrated controlled microvortex patterns at Re=30, 75, 150. The patterns exhibited very good agreement between simulations and images. In simulation, the color map represents mass fraction of the polymer and lipid streams. In visualization, the central stream has a 10% black ink diluted with deionized water. The scale bar is 200 μm.

FIGS. 12A and 12B are graphs showing the size (12A) and polydispersity (12B) of rHDL and μHDL.

FIG. 13 is a graph showing μHDL uptake by macrophages over time. Error bar is standard deviation. N=4.

DETAILED DESCRIPTION OF THE INVENTION

I. Definitions

Figure 2:
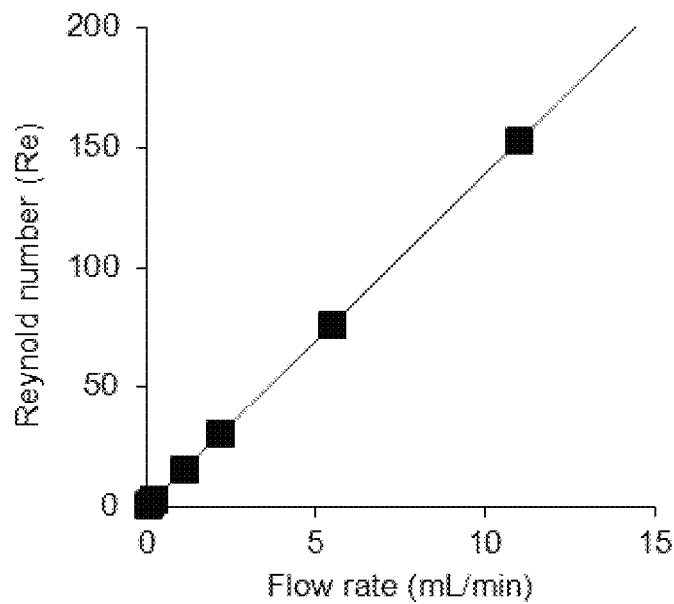
FIG. 2 is a graph showing the Reynolds number as a function of flow rate.

"Approximately" or "about", as used herein, means within a range of 5%, 10%, 15%, or 20% in either direction (greater than or less than) of the number unless otherwise stated or otherwise evident from the context (except where such number would be less than 0% or exceed 100% of a possible value).

"Nanoparticle", as used herein, refers to any entity having a diameter of less than 100 microns (μm). Typically, particles have a greatest dimension (e.g., diameter) of 1000 nm or less. In some embodiments, particles have a diameter of 300 nm or less. In some embodiments, nanoparticles have a diameter of 200 nm or less. In some embodiments, nanoparticles have a diameter of 100 nm or less. In general, particles are greater in size than the renal excretion limit, but are small enough to avoid accumulation in the liver. Nanoparticles having a spherical shape are generally referred to as "nanospheres".

"Mean particle size," as used herein, generally refers to the statistical mean particle size (diameter) of the particles in a population of particles. The diameter of an essentially spherical particle may be referred to as the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution," are used interchangeably herein and describe a plurality of liposomal nanoparticles or microparticles where the particles have the same or nearly the same diameter or aerodynamic diameter. As used herein, a monodisperse distribution refers to particle distributions in which 75, 76, 77, 78, 79, 80, 81, 82, 83, 84, 85, 86, 86, 88, 89, 90, 91, 92, 93, 94, 95% or greater of the distribution lies within 85, 80, 75, 70, 65, 60, 55, 50, 45, 40, 35, 30, 25, 20, 15, or 10% of the mass median diameter or aerodynamic diameter.

In some embodiments, a population of particles may be relatively uniform in terms of size, shape, charge, and/or composition. In general, the particles are biodegradable and/or biocompatible. The particles can be solid or hollow and can contain one or more layers. In some embodiments, the particles are spheres, spheroids, flat, plate-shaped, cubes, cuboids, ovals, ellipses, cylinders, cones, or pyramids. In some embodiments, particles can contain a matrix of one or more polymers. In some embodiments, the matrix is cross-linked. In some embodiments, formation of the matrix involves a cross-linking step. In some embodiments, the matrix is not substantially cross-linked. In some embodiments, formation of the matrix does not involve a cross-linking step.

In certain embodiments, the particles are organic particles such as particles made from organic polymer, lipids, sugars, or other organic materials. Such organic particles may optionally contain some inorganic material; however, the amount of inorganic material is less than 50%, less than 25%, less than 10%, less than 5%, or less than 1%. In certain embodiments, the particles are polymeric particles with a substantial portion of the matrix of the particle being polymeric. In other embodiments, the particles formed from lipids, such as phospholipids.

"Small molecule", as used herein, generally refers to an organic molecule that is less than about 2000 g/mol in size. In some embodiments, the small molecule is less than about 1500 g/mol or less than about 1000 g/mol. In some embodiments, the small molecule is less than about 800 g/mol or less than about 500 g/mol. In some embodiments, small molecules are non-polymeric and/or non-oligomeric. In some embodiments, small molecules are not proteins, peptides, or amino acids. In some embodiments, small molecules are not nucleic acids or nucleotides. In some embodiments, small molecules are not saccharides or polysaccharides.

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties.

"Hydrophobic" as used herein refers to substances that lack an affinity for water; tending to repel and not absorb water as well as not dissolve in or mix with water.

"Pharmaceutically acceptable," as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

"Biocompatible" as used herein, generally refer to materials that are, along with any metabolites or degradation products thereof, generally nontoxic to the recipient, and do not cause any significant adverse effects to the recipient. Generally speaking, biocompatible materials are materials which do not elicit a significant inflammatory or immune response when administered to a patient.

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

The term "therapeutic agent" refers to an agent that can be administered to prevent or treat a disease or disorder. Therapeutic agents can be a nucleic acid, a nucleic acid analog, a small molecule, a peptidomimetic, a protein, peptide, carbohydrate or sugar, lipid, or surfactant, or a combination thereof.

The term "treating" or preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "therapeutically effective amount" refers to an amount of the therapeutic agent that, when incorporated into and/or onto particles described herein, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The terms "incorporated" and "encapsulated" refers to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including, for example: attached to a monomer of such polymer (by covalent, ionic, or other binding interaction), physical admixture, enveloping the agent in a coating layer of polymer, incorporated into the polymer, distributed throughout the polymeric matrix, appended to the surface of the polymeric matrix (by covalent or other binding interactions), encapsulated inside the polymeric matrix, etc. The term "co-incorporation" or "co-encapsulation" refers to-the incorporation of a therapeutic agent or other material and at least one other therapeutic agent or other material in a subject composition.

As used herein, the term "subject" or "patient" refers to any organism to which particles produced by a microfluidic system as described herein may be administered, e.g. for experimental, therapeutic, diagnostic, and/or prophylactic purposes. Typical subjects include animals (e.g., mammals such as mice, rats, rabbits, non-human primates, and humans) and/or plants.

The term "targeting moiety" as used herein refers to a moiety that localizes to or away from a specific locale. The moiety may be, for example, a protein, nucleic acid, nucleic acid analog, carbohydrate, or small molecule. Said entity may be, for example, a therapeutic compound such as a small molecule, or a diagnostic entity such as a detectable label. Said locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

II. Method of Producing Particles

Methods of producing particles using a microfluidic device are described herein. The methods involve creating three-dimensional (3D) combined-flow-interface patterns in multi-lane fluidic devices. "Multilane", as used herein, refers to a main fluidic channel having multiple fluid-stream inlets. The inlets can be any arrangement, direction, and/or orientation provided they create the necessary flow patterns to form particles. In some embodiments, the configuration is a t-shaped configuration, wherein the angle between inlets is 90 degrees. Other configurations where the angle between inlets is less than 90 degrees can also be used.

The 3D-pattern can be varied as a function of one or more of the geometry of the inlets to a main fluidic channel in which the 3D-pattern is formed, the Reynolds number of the flows, the dimensions of the main fluidic channel and the inlets, and the spacing of adjacent inlets. In some embodiments, 3D combined-flow-interface patterns are created using a three-lane fluidic device having a fixed inlet geometry. Exemplary devices are described in U.S. Patent Application Publication No. 20130014828 to Kim et al.

The method involves mixing a solution of one or more materials that form the particle with a second solvent or solution, which is a non-solvent for the one or more materials. Upon mixing, the at least two solutions/solvents form a three-dimensional pattern containing at least two symmetrical microvortices that form simultaneously. The particles are formed at the interface of the two solutions.

A. Polymeric Particles

In some embodiments, the particles are polymeric nanoparticles formed by mixing a solution containing a polymer with a non-solvent for the polymer. In specific embodiments, the polymer is introduced as a solution in an organic solvent and the non-solvent is water or an aqueous solution The polymer can be a naturally occurring polymer, a semi-synthetic polymer, or a synthetic polymer. In some embodiments, the polymer is biocompatible. In some embodiments, the polymer is biocompatible and non-degradable. In other embodiments, the polymer is biocompatible and biodegradable.

Any polymer may be used in the methods described herein. Polymers may be homopolymers or copolymers containing two or more monomers. In terms of sequence, copolymers may be random, block, graft, or contain a combination of random, block, and/or graft sequences. In some embodiments, block copolymers are diblock copolymers. In some embodiments, block copolymers are triblock copolymers. In some embodiments, polymers can be linear or branched polymers. In some embodiments, the polymer(s) can be in the form of a blend, mixture, and/or adduct of any of the polymers described herein.

Exemplary polymers include, but are not limited to, polyalkylenes (e.g. polyethylenes), polycarbonates (e.g. poly(1,3-dioxan-2one)), polyanhydrides (e.g. poly(sebacic anhydride)), polyhydroxyacids (e.g. poly(.beta.-hydroxyalkanoate)), polyfumarates, polycaprolactones, polyamides (e.g. polycaprolactam), polyacetals, polyethers, polyesters (e.g. polylactide, polyglycolide), poly(orthoesters), polyvinyl alcohols, polyurethanes, polyphosphazenes, polyacrylates, polymethacrylates, polycyanoacrylates, polyureas, polystyrenes, and polyamines.

In some embodiments, polymers include polymers which have been approved for use in humans by the U.S. Food and Drug Administration (FDA) under 21 C.F.R. § 177.2600, including but not limited to polyesters (e.g. polylactic acid, polyglycolic acid, poly(lactic-co-glycolic acid), polycaprolactone, polyvalerolactone, poly(1,3-dioxan-2one)); polyanhydrides (e.g. poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may contain anionic groups (e.g. phosphate group, sulphate group, carboxylate group); cationic groups (e.g. quaternary amine group); or polar groups (e.g. hydroxyl group, thiol group, amine group). In some embodiments, polymers can be hydrophobic. In some embodiments, polymers can be cationic. In some embodiments, polymers can be anionic. In some embodiments, polymers can be of neutral charge.

In some embodiments, polymers may be modified with one or more moieties and/or functional groups. Any moiety or functional group can be used. In some embodiments, polymers may be modified with polyethylene glycol (PEG), with a carbohydrate, and/or with acyclic polyacetals derived from polysaccharides. In certain embodiments, a polymer may be a copolymer of PEG.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers containing lactic acid and glycolic acid units, such as poly(lactic acid-co-glycolic acid) and poly(lactide-co-glycolide), collectively referred to herein as "PLGA"; and homopolymers containing glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; copolymers of PLGA and PEG; polymers and copolymers of lactide and glycolide (e.g. copolymers of PLA and PEG, copolymers of PGA and PEG, copolymers of PLGA and PEG, and derivatives thereof). In some embodiments, the polymer is a copolymer of polyethylene glycol and PLGA. In some embodiments, polymers include, for example, polyanhydrides; poly(ortho ester); copolymers of poly(ortho ester) and PEG; poly(caprolactone); copolymers of poly(caprolactone) and PEG; polylysine; copolymers of polylysine and PEG; poly(ethylene imine); copolymers of poly(ethylene imine) and PEG; poly(L-lactide-co-L-lysine); poly(serine ester); poly(4-hydroxy-L-proline ester); poly[.alpha.-(4-aminobutyl)-L-glycolic acid]; and derivatives thereof.

In some embodiments, the polymer is PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 65:35, approximately 50:50, approximately 40:60, approximately 25:75, or approximately 15:85.

In some embodiments, the polymer is one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations containing one or more of the foregoing polymers. The acrylic polymer may contain fully-polymerized copolymers of acrylic and methacrylic acid esters with a low content of quaternary ammonium groups.

In some embodiments, the polymer is a carbohydrate. In some embodiments, a carbohydrate is a polysaccharide containing simple sugars (or their derivatives) connected by glycosidic bonds, as known in the art. In some embodiments, a carbohydrate is one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan.

In some embodiments, the polymer may be a protein or peptide. Exemplary proteins that may be used in accordance with the present invention include, but are not limited to, albumin, collagen, etc.

B. Lipid Particles

The methods described herein can also be used to prepare particles formed of non-polymeric materials, such as lipids. Lipids are naturally occurring, synthetic, or semi-synthetic molecules that include fats, waxes, sterols, fat-soluble vitamins (such as vitamins A, D, E, and K), monoglycerides, diglycerides, triglycerides, phospholipids, and others.

Lipids may be broadly defined as hydrophobic or amphiphilic small molecules. Biological lipids originate entirely or in part from two distinct types of biochemical subunits or "building-blocks": ketoacyl and isoprene groups. Using this approach, lipids may be divided into eight categories: fatty acids, glycerolipids, glycerophospholipids, sphingolipids, saccharolipids, and polyketides (derived from condensation of ketoacyl subunits); and sterol lipids and prenol lipids (derived from condensation of isoprene subunits).

1. Fatty Acids

Fatty acids, or fatty acid residues when they form part of a lipid, are a diverse group of molecules which can be prepared synthetically or synthesized naturally by chain-elongation of an acetyl-CoA primer with malonyl-CoA or methylmalonyl-CoA groups in a process called fatty acid synthesis. Fatty acids are made of a hydrocarbon chain that terminates with a carboxylic acid group; this arrangement confers the molecule with a polar, hydrophilic end, and a nonpolar, hydrophobic end that is insoluble in water. The carbon chain, typically between four and 24 carbons long, may be saturated or unsaturated, and may be attached to functional groups containing oxygen, halogens, nitrogen, and sulfur. Where a double bond exists, there is the possibility of either a cis or trans geometric isomerism, which significantly affects the molecule's configuration. Cis-double bonds cause the fatty acid chain to bend, an effect that is compounded with more double bonds in the chain. Most naturally occurring fatty acids are of the cis configuration, although the trans form does exist in some natural and partially hydrogenated fats and oils. Other major lipid classes in the fatty acid category are the fatty esters and fatty amides.

2. Glycerolipids

Glycerolipids are composed mainly of mono-, di-, and tri-substituted glycerols, the most well-known being the fatty acid triesters of glycerol, called triglycerides. The word "triacylglycerol" is sometimes used synonymously with "triglyceride", though the latter lipids contain no hydroxyl group. In these compounds, the three hydroxyl groups of glycerol are each esterified, typically by different fatty acids.

Additional subclasses of glycerolipids are represented by glycosylglycerols, which are characterized by the presence of one or more sugar residues attached to glycerol via a glycosidic linkage. Examples of structures in this category are the digalactosyldiacylglycerols found in plant membranes and seminolipid from mammalian sperm cells.

3. Glycerophospholipids

Glycerophospholipids, usually referred to as phospholipids, are ubiquitous in nature and are key components of the lipid bilayer of cells, as well as being involved in metabolism and cell signaling. Most phospholipids contain a diglyceride, a phosphate group, and a simple organic molecule such as choline; one exception to this rule is sphingomyelin, which is derived from sphingosine instead of glycerol.

The structure of the phospholipid molecule generally consists of hydrophobic tails and a hydrophilic head. The 'head' is attracted to water, while the hydrophobic 'tails' are repelled by water and are forced to aggregate. The hydrophilic head contains the negatively charged phosphate group, and may contain other polar groups. The hydrophobic tail usually consists of long fatty acid hydrocarbon chains. When placed in water, phospholipids form a variety of structures depending on the specific properties of the phospholipid. Lipid bilayers occur when hydrophobic tails line up against one another, forming a membrane of hydrophilic heads on both sides facing the water.

Glycerophospholipids may be subdivided into distinct classes, based on the nature of the polar headgroup at the sn-3 position of the glycerol backbone in eukaryotes and eubacteria, or the sn-1 position in the case of archaebacteria. Examples of glycerophospholipids found in biological membranes are phosphatidylcholine (also known as PC, GPCho or lecithin), phosphatidylethanolamine (PE or GPEtn) and phosphatidylserine (PS or GPSer).

In eukaryotes, phospholipids are generally classified into two types: diacylglycerides and phosphingolipids. Examples of diacylglycerides include, but are not limited to, phosphatidic acid (phosphatidate) (PA), phosphatidylethanolamine (cephalin) (PE), phosphatidylcholine (lecithin) (PC), phosphatidylserine (PS), and phosphoinositides, such as phosphatidylinositol (PI), phosphatidylinositol phosphate (PIP), phosphatidylinositol bisphosphate (PIP2) and, phosphatidylinositol triphosphate (PIPS). Examples of phospingolipids include, but are not limited to, ceramide phosphorylcholine (Sphingomyelin) (SPH), ceramide phosphorylethanolamine (Sphingomyelin) (Cer-PE), and Ceramide phosphoryllipid.

Other phospholipids that can be used are shown in Table 1 below.

TABLE 1

| | | Phospholipids | |
|---|---|---|---|
| Abbreviation | CAS No. | Name | Type |
| DDPC | 3436-44-0 | 1,2-Didecanoyl-sn-glycero-3-phosphocholine | Phosphatidylcholine |
| DEPA-NA | 80724-31-8 | 1,2-Dierucoyl-sn-glycero-3-phosphate (Sodium Salt) | Phosphatidic acid |
| DEPC | 56649-39-9 | 1,2-Dierucoyl-sn-glycero-3-phosphocholine | Phosphatidylcholine |
| DEPE | 988-07-2 | 1,2-Dierucoyl-sn-glycero-3-phosphoethanolamine | Phosphatidylethanolamine |
| DEPG-NA | | 1,2-Dierucoyl-sn-glycero-3[Phospho-rac-(1-glycerol . . .) (Sodium Salt) | Phosphatidylglycerol |
| DLOPC | 998-06-1 | 1,2-Dilinoleoyl-sn-glycero-3-phosphocholine | Phosphatidylcholine |
| DLPA-NA | | 1,2-Dilauroyl-sn-glycero-3-phosphate (Sodium Salt) | Phosphatidic acid |
| DLPC | 18194-25-7 | 1,2-Dilauroyl-sn-glycero-3-phosphocholine | Phosphatidylcholine |
| DLPE | | 1,2-Dilauroyl-sn-glycero-3-phosphoethanolamine | Phosphatidylethanolamine |
| DLPG-NA | | 1,2-Dilauroyl-sn-glycero-3[Phospho-rac-(1-glycerol . . .) (Sodium Salt) | Phosphatidylglycerol |
| DLPG-NH4 | | 1,2-Dilauroyl-sn-glycero-3[Phospho-rac-(1-glycerol . . .) (Ammonium Salt) | Phosphatidylglycerol |
| DLPS-NA | | 1,2-Dilauroyl-sn-glycero-3-phosphoserine (Sodium Salt) | Phosphatidylserine |
| DMPA-NA | 80724-3 | 1,2-Dimyristoyl-sn-glycero-3-phosphate (Sodium Salt) | Phosphatidic acid |
| DMPC | 18194-24-6 | 1,2-Dimyristoyl-sn-glycero-3-phosphocholine | Phosphatidylcholine |
| DMPE | 988-07-2 | 1,2-Dimyristoyl-sn-glycero-3-phosphoethanolamine | Phosphatidylethanolamine |
| DMPG-NA | 67232-80-8 | 1,2-Dimyristoyl-sn-glycero-3[Phospho-rac-(1-glycerol . . .) (Sodium Salt) | Phosphatidylglycerol |
| DMPG-NH4 | | 1,2-Dimyristoyl-sn-glycero-3[Phospho-rac-(1-glycerol . . .) (Ammonium Salt) | Phosphatidylglycerol |
| DMPG-NH4/NA | | 1,2-Dimyristoyl-sn-glycero-3[Phospho-rac-(1-glycerol . . .) (Sodium/Ammonium Salt) | Phosphatidylglycerol |
| DMPS-NA | | 1,2-Dimyristoyl-sn-glycero-3-phosphoserine (Sodium Salt) | Phosphatidylserine |
| DOPA-NA | | 1,2-Dioleoyl-sn-glycero-3-phosphate (Sodium Salt) | Phosphatidic acid |
| DOPC | 4235-95-4 | 1,2-Dioleoyl-sn-glycero-3-phosphocholine | Phosphatidylcholine |
| DOPE | 4004-5-1- | 1,2-Dioleoyl-sn-glycero-3-phosphoethanolamine | Phosphatidylethanolamine |

TABLE 1-continued

| Phospholipids | | | |
|---|---|---|---|
| Abbreviation | CAS No. | Name | Type |
| DOPG-NA | 62700-69-0 | 1,2-Dioleoyl-sn-glycero-3[Phospho-rac-(1-glycerol . . .) (Sodium Salt) | Phosphatidylglycerol |
| DOPS-NA | 70614-14-1 | 1,2-Dioleoyl-sn-glycero-3-phosphoserine (Sodium Salt) | Phosphatidylserine |
| DPPA-NA | 71065-87-7 | 1,2-Dipalmitoyl-sn-glycero-3-phosphate (Sodium Salt) | Phosphatidic acid |
| DPPC | 63-89-8 | 1,2-Dipalmitoyl-sn-glycero-3-phosphocholine | Phosphatidylcholine |
| DPPE | 923-61-5 | 1,2-Dipalmitoyl-sn-glycero-3-phosphoethanolamine | Phosphatidylethanolamine |
| DPPG-NA | 67232-81-9 | 1,2-Dipalmitoyl-sn-glycero-3[Phospho-rac-(1-glycerol . . .) (Sodium Salt) | Phosphatidylglycerol |
| DPPG-NH4 | 73548-70-6 | 1,2-Dipalmitoyl-sn-glycero-3[Phospho-rac-(1-glycerol . . .) (Ammonium Salt) | Phosphatidylglycerol |
| DPPS-NA | | 1,2-Dipalmitoyl-sn-glycero-3-phosphoserine (Sodium Salt) | Phosphatidylserine |
| DSPA-NA | 108321-18-2 | 1,2-Distearoyl-sn-glycero-3-phosphate (Sodium Salt) | Phosphatidic acid |
| DSPC | 816-94-4 | 1,2-Distearoyl-sn-glycero-3-phosphocholine | Phosphatidylcholine |
| DSPE | 1069-79-0 | 1,2-Distearoyl-sn-glycero-3-phosphoethanolamine | Phosphatidylethanolamine |
| DSPG-NA | 67232-82-0 | 1,2-Distearoyl-sn-glycero-3[Phospho-rac-(1-glycerol . . .) (Sodium Salt) | Phosphatidylglycerol |
| DSPG-NH4 | 108347-80-4 | 1,2-Distearoyl-sn-glycero-3[Phospho-rac-(1-glycerol . . .) (Ammonium Salt) | Phosphatidylglycerol |
| DSPS-NA | | 1,2-Distearoyl-sn-glycero-3-phosphoserine (Sodium Salt) | Phosphatidylserine |
| Egg Sphingomyelin | | Egg-PC | Phosphatidylcholine |
| empty Liposome EPC | | | |
| HEPC | | Hydrogenated Egg PC | Phosphatidylcholine |
| HSPC | | High purity Hydrogenated Soy PC | Phosphatidylcholine |
| HSPC | | Hydrogenated Soy PC | Phosphatidylcholine |
| LYSOPC MYRISTIC | 18194-24-6 | 1-Myristoyl-sn-glycero-3-phosphocholine | Lysophosphatidylcholine |
| LYSOPC PALMITIC | 17364-16-8 | 1-Palmitoyl-sn-glycero-3-phosphocholine | Lysophosphatidylcholine |
| LYSOPC STEARIC | 19420-57-6 | 1-Stearoyl-sn-glycero-3-phosphocholine | Lysophosphatidylcholine |
| Milk Sphingomyelin MPPC | | 1-Myristoyl-2-palmitoyl-sn-glycero 3-phosphocholine | Phosphatidylcholine |
| MSPC | | 1-Myristoyl-2-stearoyl-sn-glycero-3-phosphocholine | Phosphatidylcholine |
| PMPC | | 1-Palmitoyl-2-myristoyl-sn-glycero-3-phosphocholine | Phosphatidylcholine |
| POPC | 26853-31-6 | 1-Palmitoyl-2-oleoyl-sn-glycero-3-phosphocholine | Phosphatidylcholine |
| POPE | | 1-Palmitoyl-2-oleoyl-sn-glycero-3-phosphoethanolamine | Phosphatidylethanolamine |
| POPG-NA | 81490-05-3 | 1-Palmitoyl-2-oleoyl-sn-glycero-3[Phospho-rac-(1-glycerol). . .] (Sodium Salt) | Phosphatidylglycerol |
| PSPC | | 1-Palmitoyl-2-stearoyl-sn-glycero-3-phosphocholine | Phosphatidylcholine |
| SMPC | | 1-Stearoyl-2-myristoyl-sn-glycero-3-phosphocholine | Phosphatidylcholine |
| SOPC | | 1-Stearoyl-2-oleoyl-sn-glycero-3-phosphocholine | Phosphatidylcholine |
| SPPC | | 1-Stearoyl-2-palmitoyl-sn-glycero-3-phosphocholine | Phosphatidylcholin |

In some embodiments, the lipid component is one or more phospholipids. In some embodiments, the lipid is, or contains, DMPC or MHPC.

4. Sphingolipids

Sphingolipids are a complicated family of compounds that share a common structural feature, a sphingoid base backbone that is synthesized de novo from the amino acid serine and a long-chain fatty acyl CoA, then converted into ceramides, phosphosphingolipids, glycosphingolipids and other compounds. The major sphingoid base of mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms.

The major phosphosphingolipids of mammals are sphingomyelins (ceramide phosphocholines), whereas insects contain mainly ceramide phosphoethanolamines and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides.

5. Sterol Lipids

Sterol lipids, such as cholesterol and its derivatives, are an important component of membrane lipids, along with the glycerophospholipids and sphingomyelins. The steroids are all derived from the same fused four-ring core structure. Other examples of sterols are the bile acids and their conjugates. The plant equivalents are the phytosterols, such as β-sitosterol, stigmasterol, and brassicasterol.

6. Prenol Lipids

Prenol lipids are synthesized from the five-carbon-unit precursors isopentenyl diphosphate and dimethylallyl diphosphate. The simple isoprenoids (linear alcohols, diphosphates, etc.) are formed by the successive addition of C5 units, and are classified according to number of these terpene units. Structures containing greater than 40 carbons are known as polyterpenes. Carotenoids are important simple isoprenoids that function as antioxidants and as precursors of vitamin A. Another biologically important class of molecules is exemplified by the quinones and hydroquinones, which contain an isoprenoid tail attached to a quinonoid core of non-isoprenoid origin. Vitamin E and vitamin K, as well as the ubiquinones, are examples of this class. Prokaryotes synthesize polyprenols (called bactoprenols) in which the terminal isoprenoid unit attached to oxygen remains unsaturated, whereas in animal polyprenols (dolichols) the terminal isoprenoid is reduced.

7. Saccharolipids

Saccharolipids describe compounds in which fatty acids are linked directly to a sugar backbone, forming structures that are compatible with membrane bilayers. In the saccharolipids, a monosaccharide substitutes for the glycerol backbone present in glycerolipids and glycerophospholipids. The most familiar saccharolipids are the acylated glucosamine precursors of the Lipid A component of the lipopolysaccharides in Gram-negative bacteria. Typical lipid A molecules are disaccharides of glucosamine, which are derivatized with as many as seven fatty-acyl chains.

The lipid particles can be prepared in a manner similar to polymeric particles or polymer-lipid hybrid (PLH) particles. The lipids are dissolved in suitable solvent, such as methanol, ethanol, or chloroform, and mixed with a non-solvent for the lipid. In some embodiments, the microfluidic device has three inlet channels with rectangular cross-sections of dimensions 200 μm wide, 400 μm high, and 10 mm long. These inlet channels converged to form a single outlet channel of rectangular cross-section with dimensions 2000 μm wide, 400 μm high, and 20 mm long. The device can be fabricated with a variety of materials, such as polydimethylsiloxane (PDMS) (SYLGARD 184, Dow Corning, Midland, Mich.) using standard soft-lithography techniques.

HDL-mimicking nanomaterials (μHDL, DiO-μHDL, [s]-μHDL, Au-μHDL, FeO-μHDL, and QD-μHDL) were reconstituted using a single-step, self-assembly method in a single layer, 3-inlet microfluidic device. The microfluidic device can generate tunable dual microvortices and a focusing pattern at Reynolds number (Re) ~150 allowing rapid and effective mixing of the solutions in the central inlet and the two outer inlets. The type or composition of the phospholipids as well as the mixing conditions with apoA-I can be varied by tuning the microvortex patterns in the microfluidic device. The solvent of the central inlet can be chosen in view of the lipophilicity of the individual imaging agent payloads.

The self-assembly process in this microfluidic approach occurs due to: (1) the transition of the lipid/payload from an organic solution to an aqueous one, which initiates the formation of lipid aggregates, and (2) the microvortices cause apoA-I to swiftly incorporate in the nascent aggregates, resulting in instantaneous formation of small μHDL nanoparticles. While a typical conventional synthesis typically requires the formation of vesicles via lipid film hydration and subsequent 1 hr sonication and 16 hr incubation with apoA-I, resulting in typical batch sizes of 120 mg, the HDL production productivity using the microfluidic approach is continuous at a rate of at least 100, 125, 150, 165, 200, 225, 250, 275, 300, 325, 350, 375, 400, or 420 mg/hr.

The diameter of the particles for a given lipid-to-protein ratio (i.e. DMPC/apoA-I=2.5) can be controlled by varying the flow rate of each inlet (i.e. Reynolds number). For example, the average particle size of μHDL decreases from 30.0 nm to 8.1 nm by increasing the Reynolds number from approximately 30 to 150. The average size can also change as a function of the DMPC:apoA-I ratio1. The average size of μHDL remained 7.6~8.5 nm as the DMPC:apoA-I ratio increased from 0.625 to 2.5 but increased to approximately 30.6 nm as this ratio increased from 2.5 to 12.5. The polydispersity of rHDL gradually decreased as the Reynolds number increased, and did not show any significant difference before and after the purification process. Also, the polydispersity remained 0.094~0.102 but increased up to 0.218 as the DMPC-apoA-I ratio increased.

The structure of rHDL reconstituted using conventional multi-step methods was compared with that of μHDL using transmission electron microscopy (TEM). The discoidal shape and characteristic rouleaux structures (stacks of discs on their edge) were observed for both. Dynamic light scattering showed that the average size was not significantly different and was 8-9 nm for both methods, while μHDL had reduced polydispersity compared to the rHDL.

C. Polymer-Lipid Hybrid Particles

In some embodiments, the particles are polymer-lipid hybrid (PLH) particles. Suitable polymers and lipids include those discussed above. Exemplary lipids include, but are not limited to, lecithin, 1,2-distearoyl-sn-glycero-3-phosphoethanolamine-N-[amino(polyethylene glycol)], dimyristoylphosphatidylcholine (DMPC), 1,2-dihexanoyl-sn-glycero-3-phosphocholine (DHPC), 1-myristoyl-2-hydroxy-sn-glycero-phosphocholine (MHPC), and combinations thereof. The polymer and lipid can be in any configuration.

For example, in some embodiments, the particle contains a polymeric core and the lipid is a coating on the particle, such as coating of HDL.

PLH nanoparticles can be synthesized by rapidly mixing an organic solution of a polymer, such as PLGA, dissolved in an organic solvent, such as acetonitrile, in the central inlet and an aqueous solution containing the lipid, such as 4% ethanol aqueous solution containing lecithin (lipid) and DSPE-PEG (lipid-PEG) in the outer inlets in a single layer, 3-inlet microfluidic channel Microvortices were generated at a relatively higher Reynolds number regime (Re~75) than used in conventional microfluidics (Re~1). The nanoparticles synthesized in the microvortices have a polymeric core (e.g., PLGA) and a lipid corona (e.g., lecithin and DSPE-PEG). These hybrid nanoparticles combine the unique strengths of liposomal and polymeric nanoparticles while overcoming their limitations in terms of drug encapsulation efficiency and storage stability. Compared to pure PLGA-PEG nanoparticles these lipid-polymer hybrid nanoparticles exhibit a higher drug loading and slower drug release.

Symmetric microvortices are created at the intersection of the three inlets. The upstream profiles show the inner shapes of two symmetric microvortices, which results in rapid mixing of polymer and lipid (or non-solvent). The downstream patterns exhibit 3D diamond-like focusing patterns that can prevent polymer aggregation near the channel walls, preventing the channel from clogging. The use of microvortices enabled up to 1000 times higher productivity than previous approaches using diffusive mixing and convective mixing. For example, the amount of PLGA included in the nanoparticles produced in this platform could be varied by altering the Reynolds number (Re) (i.e. flow rate) under a given PLGA concentration of 5 mg/mL. The size of monodisperse PLH nanoparticles was controlled by varying the Reynolds number, while maintaining all other synthesis parameters constant. For example, the nanoparticle size was decreased from 81 to 55 nm by increasing the Reynolds number from 75 to 150 with a constant PLGA-lipid weight ratio of 10. Dynamic light scattering (DLS) revealed the average sizes of these nanoparticles to be 55 nm and 81 nm for Re=150 and Re=75, respectively. Their low polydispersity of ~0.1 revealed a uniform size distribution. Transmission electron microscopy (TEM) allowed us to qualitatively assess their characteristics.

The methods described herein can be produced at a rate significantly faster than prior art methods. In some embodiments, the particles are produce at a rate greater than 0.025, 0.05, 0.1, 0.15, 0.2, 0.25, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, or 4.0 grams of particles per hour of fluid flow.

The methods can be used to control the particle size of the resulting particles. In some embodiments, the particles have an average largest dimension of about 5 nm and about 200 nm, about 5 nm to about 150 nm, about 5 nm to about 100 nm.

D. Therapeutic, Diagnostic, Prophylactic, and Nutriceutical Agents

In some embodiments, the fluid streams may optionally contain one or more agents (including drugs, diagnostic agents, prophylactic and/or nutriceutical agents) to be associated with the surface of, encapsulated within, surrounded by, and/or dispersed throughout the particles produced using the methods described herein.

The particles may provide controlled release of the drug. For example, the unaltered particles may provide release of an effective amount of the drug over time based on the rate of diffusion of the drug form the particle and/or the rate of degradation of the polymer. The composition of the particle (e.g., polymer, lipid, etc.) can be varied to manipulate the degradation behavior of the polymer and thus the release rate/time of the agent to be delivered. Alternatively, the particle can be coated with one or more materials to provide controlled release, such as sustained release or delayed release of the agent or agents to be delivered.

Exemplary therapeutic agents include, but are not limited to, small molecules, organometallic compounds, nucleic acids, proteins (including multimeric proteins, protein complexes, etc.), peptides, lipids, carbohydrates, hormones, metals, radioactive elements and compounds, drugs, vaccines, immunological agents, etc., and/or combinations thereof.

In some embodiments, the therapeutic agent is a small molecule and/or organic compound with pharmaceutical activity. In some embodiments, the therapeutic agent is a clinically-used drug. In some embodiments, the drug is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, .beta.-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitor of DNA, RNA, or protein synthesis, etc.

Exemplary therapeutic agents that can be incorporated into the particles include, but are not limited to. tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasitics (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the particles into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A.

The particles may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

Exemplary diagnostic agents include paramagnetic molecules, fluorescent compounds, magnetic molecules, and radionuclides, x-ray imaging agents, and contrast agents. Diagnostic agents include commercially available imaging agents used in positron emissions tomography (PET), computer assisted tomography (CAT), single photon emission computerized tomography, x-ray, fluoroscopy, and magnetic resonance imaging (MRI); anti-emetics; and contrast agents.

Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, a diagnostic and/or therapeutic agent may be a radionuclide. Among the radionuclides used, gamma-emitters, positron-emitters, and X-ray emitters are suitable for diagnostic and/or therapeutic purposes, while beta emitters and alpha-emitters may also be used for therapy. Suitable radionuclides are known in the art.

In some embodiments, a diagnostic agent may be a fluorescent, luminescent, or magnetic moiety. Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art In one embodiment, the particles are polymeric particles or polymeric-lipid hybrid (PLH) having encapsulated therein one or more therapeutic, prophylactic, and/or diagnostic agents. In another embodiment, the particles are lipid particles, such as phospholipid particles having encapsulated therein one or more lipoproteins, such as apoA-I (high density lipoprotein, HDL). A lipoprotein is a biochemical assembly that contains both proteins and lipids, bound to the proteins, which allow fats to move through the water inside and outside cells. The proteins serve to emulsify the lipid (otherwise called fat) molecules. Examples include the plasma lipoprotein particles classified under high-density (HDL) and low-density (LDL) lipoproteins, which enable fats to be carried in the blood stream, the transmembrane proteins of the mitochondrion and the chloroplast, and bacterial lipoproteins. Representative lipoproteins include, but are not limited to, very-low-density lipoproteins (VLDL), intermediate-density lipoproteins (IDL) are intermediate between VLDL and LDL, low-density lipoproteins (LDL), and high-density lipoproteins (HDL)

The lipoprotein can be encapsulated and/or associate with the particle alone or in combination with one or more additional agents, such as cholesterol lowering drugs (e.g., statins, fenofibrate, etc.) and/or an imaging agent, such as fluorescent hydrophobic agent (e.g., DiO).

Exemplary statins include, but are not limited to, atorvastatin, marketed as Lipitor (manufactured by Pfizer) and Torvast, fluvastatin (Lescol), lovastatin (Mevacor, Altocor, Altoprev), pitavastatin (Livalo, Pitava), pravastatin (Pravachol, Selektine, Lipostat), rosuvastatin (Crestor) and simvastatin (Zocor, Lipex). Combinations of a statin and another agent, such as ezetimibe/simvastatin, can also be used. Other cholesterol-lowering drug classes include, but are not limited to, fibrates, niacin and derivatives thereof (e.g., acipimox), bile acid sequestrants (resins, e.g. cholestyramine), selective inhibitors of dietary cholesterol absorption (e.g., ezetimibe (Zetia)), microsomal triglyceride transfer protein (MTP) inhibitors (e.g., lomitapide (Juxtapid)), phytosterols, and orlistat (Xenical).

In some embodiments, particles produced using the methods described here in contain less than 80%, less then 75%, less than 70%, less than 60%, less than 50% by weight, less than 40% by weight, less than 30% by weight, less than 20% by weight, less than 15% by weight, less than 10% by weight, less than 5% by weight, less than 1% by weight, less than 0.5% by weight, or less than 0.1% by weight of the agent. In some embodiments, the agent may be a mixture of pharmaceutically active agents. The agent or agents can be introduced in the polymer solution, the non-solvent/lipid solution, or both.

E. Targeting Moieties

In some embodiments, the particles can be functionalized with one or more targeting moieties, such as cell-type or cell-state specific targeting domain or targeting signal. Examples of moieties which may be linked or unlinked to the particles include, for example, targeting moieties which provide for the delivery of molecules to specific cells. The targeting signal or sequence can be specific for a host, tissue, organ, cell, organelle, non-nuclear organelle, or cellular compartment. For example, the compositions disclosed herein can be modified with galactosyl-terminating macromolecules to target the compositions to the liver or to liver cells. The modified compositions selectively enter hepatocytes after interaction of the carrier galactose residues with the asialoglycoprotein receptor present in large amounts and high affinity only on these cells. Moreover, the compositions disclosed here can be targeted to other specific intercellular regions, compartments, or cell types.

In one embodiment, the targeting signal binds to its ligand or receptor which is located on the surface of a target cell such as to bring the vector and cell membranes sufficiently close to each other to allow penetration of the vector into the cell. Additional embodiments of the present disclosure are directed to specifically delivering polynucleotides to specific tissue or cell types, wherein the polynucleotides can encode a polypeptide or interfere with the expression of a different polynucleotide. The polynucleotides delivered to the cell can encode polypeptides that can enhance or contribute to the functioning of the cell.

The targeting moiety can be an antibody or antigen binding fragment thereof, an antibody domain, an antigen, a T-cell receptor, a cell surface receptor, a cell surface adhesion molecule, a major histocompatibility locus protein, a viral envelope protein and a peptide selected by phage display that binds specifically to a defined cell.

One skilled in the art will appreciate that the tropism of the particles described can be altered by merely changing the targeting signal. It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest.

1. Nucleic Acid Targeting Moieties

As used herein, a "nucleic acid targeting moiety" is a nucleic acid that binds selectively to a target. In some embodiments, a nucleic acid targeting moiety is a nucleic acid aptamer. An aptamer is usually a polynucleotide that binds to a specific target structure that is associated with a particular organ, tissue, cell, extracellular matrix component, and/or intracellular compartment. In general, the targeting function of the aptamer is based on the three-dimensional structure of the aptamer. In some embodiments, binding of an aptamer to a target is typically mediated by the interaction between the two- and/or three-dimensional structures of both the aptamer and the target. In some embodiments, binding of an aptamer to a target is not solely based on the primary sequence of the aptamer, but depends on the three-dimensional structure(s) of the aptamer and/or target. In some embodiments, aptamers bind to their targets via complementary Watson-Crick base pairing which is interrupted by structures (e.g. hairpin loops) that disrupt base pairing.

In some embodiments, a nucleotide sequence that is homologous to a nucleic acid targeting moiety may be used. In some embodiments, a nucleotide sequence is considered to be "homologous" to a nucleic acid targeting moiety if it contains fewer than 30, 25, 20, 15, 10, 5, 4, 3, 2, or 1 nucleic acid substitutions relative to the aptamer. In some embodiments, a nucleotide sequence is considered to be "homologous" to a nucleic acid targeting moiety if their sequences are at least 25%, 30%, 35%, 40%, 45%, 50%, 55%, 60%, 65%, 70%, 75%, 80%, 85%, 90%, 95%, or 99% identical. In some embodiments, a nucleic acid sequence is considered to be "homologous" to a nucleic acid targeting moiety if their sequences are at least 25%, 30%, 35%, 40%, 45%, 50%, 55%, 60%, 65%, 70%, 75%, 80%, 85%, 90%, 95%, or 99% similar.

Nucleic acids may be prepared according to any available technique including, but not limited to chemical synthesis, enzymatic synthesis, enzymatic or chemical cleavage of a longer precursor, etc. Methods of synthesizing RNAs are known in the art (see, e.g. Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in molecular biology, v. 288 (Clifton, N.J.) Totowa, N.J.: Humana Press, 2005).

A nucleic acid that forms the nucleic acid targeting moiety may contain naturally occurring nucleosides, modified nucleosides, naturally occurring nucleosides with hydrocarbon linkers (e.g. an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid targeting moiety can be replaced with a hydrocarbon linker or a polyether linker provided that the binding affinity and selectivity of the nucleic acid targeting moiety is not substantially reduced by the substitution (e.g. the dissociation constant of the nucleic acid targeting moiety for the target should not be greater than about $1 \times 10^{-3}$ M).

Nucleic acids containing a variety of different nucleotide analogs, modified backbones, or non-naturally occurring internucleoside linkages can be utilized in accordance with the present invention. Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g. aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitropyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids containing such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. Nucleic acids may, for example, contain a modification to a sugar, nucleoside, or internucleoside linkage.

2. Small Molecule Targeting Moieties

In some embodiments, a targeting moiety may be a small molecule. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol.

Any small molecule that specifically binds to a desired target can be used. One exemplary small molecule targeting moiety is folic acid. Folic acid (i.e., pteroylglutamic acid, Vitamin B9) specifically binds to the folate receptor (FR), which is preferentially expressed in tumor tissues relative to healthy tissues (Low et al., 2004, Adv. Drug Deliv. Rev., 56:1055).

In some embodiments, small molecule targeting moieties that may be used to target cells associated with prostate cancer tumors include PSMA peptidase inhibitors, such as 2-PMPA, GPI5232, VA-033, phenylalkylphosphonamidates, and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives. In some embodiments, small molecule targeting moieties that may be used to target cells associated with prostate cancer tumors include hydroxamate derivatives. In some embodiments, small molecule targeting moieties that may be used to target cells associated with prostate cancer tumors include PBDA- and urea-based inhibitors, such as ZJ 43, ZJ 11, ZJ 17, ZJ 38 (Nan et al., 2000, J. Med. Chem., 43:772; and Kozikowski et al., 2004, J. Med. Chem., 47:1729), and/or and analogs and derivatives thereof In some embodiments, small molecule targeting moieties that may be used to target cells associated with prostate cancer tumors include androgen receptor targeting agents (ARTAs). In some embodiments, small molecule targeting moieties that may be used to target cells associated with prostate cancer tumors include polyamines, such as putrescine, spermine, and spermidine.

Tumor Targeting

In one embodiment, the targeting signal is used to selectively target tumor cells. Tumor cells express cell surface markers which may only be expressed in the tumor or present in non-tumor cells but preferentially presented in tumor cells. Such markers can be targeted to increase delivery of the particles to cancer cells.

For example, in some embodiments, the targeting moiety is a polypeptide including an arginine-glycine-aspartic acid sequence. For example, the targeting moiety can be an arginine-glycine-aspartic acid-lysine (RGDK, mRGD) other polypeptide that includes the RGD sequence and is capable of binding to tumor endothelium through the interaction of RGD with $\alpha_v\beta_3$ and $\alpha_v\beta_5$. In some embodiments, a targeting moiety includes the polypeptide sequence R/KxxR/K, where "x" is any amino acid, and which allows binding to neuropilin-1. Binding with integrins or neuropilin-1 are two approaches for improving tumor-targeted and tissue-penetrating delivery to tumors in vivo. Similar approaches have been reported to facilitate ligand-specific gene delivery in vitro and targeted gene delivery to liver, spleen, and bone marrow in vivo.

Other, exemplary tumor specific cell surface markers include, but are not limited to, alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdrl gene product), multidrug-resistance-related antigen, p170, multidrug-resistance-related antigen, prostate specific antigen (PSA), CD56, NCAM, EGFR, CD44, and folate receptor. In one embodiment, the targeting signal consists of antibodies which are specific to the tumor cell surface markers.

Antibodies

Another embodiment provides an antibody or antigen binding fragment thereof bound to the disclosed particles acts as the targeting signal.

The antibodies or antigen binding fragment thereof are useful for directing the particle to a cell type or cell state. In one embodiment, the particles are coated with a polypeptide that is an antibody binding domain, for example from a protein known to bind antibodies such as Protein A and Protein G from *Staphylococcus aureus*. Other domains known to bind antibodies are known in the art and can be substituted. The antibody binding domain links the antibody, or antigen binding fragment thereof, to the particle.

In certain embodiments, the antibody that serves as the targeting signal is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting signal includes all or part of an antibody that directs the particle to the desired target cell type or cell state. Antibodies can be monoclonal or polyclonal, but are preferably monoclonal. For human gene therapy purposes, antibodies can be derived from human genes and are specific for cell surface markers, and are produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

Brain Targeting

In one embodiment, the targeting signal is directed to cells of the nervous system, including the brain and peripheral nervous system. Cells in the brain include several types and states and possess unique cell surface molecules specific for the type. Furthermore, cell types and states can be further characterized and grouped by the presentation of common cell surface molecules.

In one embodiment, the targeting signal is directed to specific neurotransmitter receptors expressed on the surface of cells of the nervous system. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter or ligand capable of specifically binding to a neurotransmitter receptor.

In one embodiment, the targeting signal is specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example stem cells Exemplary markers specific for these cell types and states are well known in the art and include, but are not limited to CD133 and Neurosphere.

Muscle Targeting

In one embodiment, the targeting signal is directed to cells of the musculoskeletal system. Muscle cells include several types and possess unique cell surface molecules specific for the type and state. Furthermore, cell types and states can be further characterized and grouped by the presentation of common cell surface molecules.

In one embodiment, the targeting signal is directed to specific neurotransmitter receptors expressed on the surface of muscle cells. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter. Exemplary neurotransmitters expressed on muscle cells that can be targeted include but are not limited to acetycholine and norepinephrine.

In one embodiment, the targeting signal is specific to muscle cells which consist of two major groupings, Type I and Type II. These cells can be further divided by their function, location, shape, myoglobin content and pathological state. Muscle cells can also be identified by their state of differentiation, for example muscle stem cells. Exemplary markers specific for these cell types and states are well known in the art include, but are not limited to MyoD, Pax7, and MR4.

1. Linkers

In some embodiments the particles can contain a linker which binds the targeting moiety to the particle. In some embodiments, the linker can be a polypeptide, or any other suitable linker that is known in the art, for example, poly ethylene glycol (PEG).

III. Pharmaceutical Formulations

For those embodiments where the one or more therapeutic, prophylactic, and/or diagnostic agents are encapsulated within a liposomal nanoparticle and/or associated with the surface of the liposome, the percent drug loading is from about 1% to about 80%, from about 1% to about 50%, preferably from about 1% to about 40% by weight, more preferably from about 1% to about 20% by weight, most preferably from about 1% to about 10% by weight. The ranges above are inclusive of all values from 1% to 80%. For those embodiments where the agent is associated with the surface of the particle, the percent loading may be higher since the amount of drug is not limited by the methods of encapsulation. In some embodiments, the agent to be delivered may be encapsulated within a liposome and associated with the surface of the particle.

The formulations described herein contain an effective amount of liposomes ("MPPs") in a pharmaceutical carrier appropriate for administration to a mucosal surface, wherein the pharmaceutical carrier is adjusted to be hypotonic. One skilled in the art can routinely adjust tonicity of pharmaceutical carriers, once the desired tissue to be treated is identified, based on the preferred tonicity ranges described herein.

Tonicity is the 'effective osmolality' and is equal to the sum of the concentrations of the solutes which have the capacity to exert an osmotic force across the membrane. A number of different materials can be used to adjust tonicity. For example, the USP 29-NF 24 lists five excipients classified as "tonicity" agents, including dextrose, glycerin; potassium chloride; mannitol; and sodium chloride See, for example, United States Pharmacopeia Convention, Inc. *United States Pharmacopeia* 29-*National Formulary* 24. Rockville Md.: U.S. Pharmacopeia Convention, Inc.; 2005: 3261; Day, A. Dextrose. In: Rowe R C, Sheskey P J and Owen S C, eds. *Handbook of Pharmaceutical Excipients*. 5th ed. Washington D.C.: American Pharmaceutical Association; 2005: 231-233; Price J C. Glycerin. In: Rowe R C, Sheskey P J and Owen S C, eds. *Handbook of Pharmaceutical Excipients*. 5th ed. Washington D.C.: American Pharmaceutical Association; 2005: 301-303; Price J C. Glycerin. In: Rowe R C, Sheskey P J and Owen S C, eds. *Handbook of Pharmaceutical Excipients*. 5th ed. Washington D.C.: American Pharmaceutical Association; 2005: 301-303; Armstrong N A. Mannitol. In: Rowe R C, Sheskey P J and Owen S C, eds. *Handbook of Pharmaceutical Excipients*. 5th ed. Washington D.C.: American Pharmaceutical Association; 2005: 449-453; Owen S C. Sodium Chloride. In: Rowe R C, Sheskey P J and Owen S C, eds. *Handbook of Pharmaceutical Excipients*. 5th ed. Washington D.C.: American Pharmaceutical Association; 2005: 671-674. Mannitol is an example of a GRAS listed ingredient accepted for use as a food additive in Europe, included in the FDA Inactive Ingredients Database (IP, IM, IV, and SC injections; infusions; buccal, oral and sublingual tablets, powders and capsules; ophthalmic preparations; topical solutions), included in nonparenteral and parenteral medicines licensed in the UK and included in the Canadian Natural Health Products Ingredients Database. A 5.07% w/v aqueous solution is isoosmotic with serum.

Minimally hypotonic formulations, preferably ranging from 20-220 mOsm/kg, provide rapid and uniform delivery of MPP to the entire vaginal surface, with minimal risk of epithelial toxicity. There is a higher osmolality in the colon, such that vehicles with an osmolality above that of blood plasma (generally considered isotonic at ~300 mOsm/kg), leads to improvements in distribution in the colon. The range for improved colon distribution with a hypotonic vehicle in the colon is ~20 mOsm/kg-450 mOsm/kg.

A. Pulmonary Formulations

Pharmaceutical formulations and methods for the pulmonary administration of active agents to patients are known in the art.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

Formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

1. Dry Powder Formulations

Dry powder formulations are finely divided solid formulations containing liposome carriers which are suitable for pulmonary administration. Dry powder formulations include, at a minimum, one or more liposome carriers which are suitable for pulmonary administration. Such dry powder formulations can be administered via pulmonary inhalation to a patient without the benefit of any carrier, other than air or a suitable propellant.

In other embodiments, the dry powder formulations contain one or more liposome gene carriers in combination with a pharmaceutically acceptable carrier. In these embodiments, the liposome gene carriers and pharmaceutical carrier can be formed into nano- or microparticles for delivery to the lung.

The pharmaceutical carrier may include a bulking agent or a lipid or surfactant. Natural surfactants such as dipalmitoylphosphatidylcholine (DPPC) are the most preferred. Synthetic and animal derived pulmonary surfactants include Exosurf—a mixture of DPPC with hexadecanol and tyloxapol added as spreading agents, Pumactant (Artificial Lung Expanding Compound or ALEC)—a mixture of DPPC and PG, KL-4—composed of DPPC, palmitoyl-oleoyl phosphatidylglycerol, and palmitic acid, combined with a 21 amino acid synthetic peptide that mimics the structural characteristics of SP-B, Venticute—DPPC, PG, palmitic acid and recombinant SP-C, Alveofact—extracted from cow lung lavage fluid, Curosurf—extracted from material derived from minced pig lung, Infasurf—extracted from calf lung lavage fluid, and Survanta—extracted from minced cow lung with additional DPPC, palmitic acid and tripalmitin. Exosurf, Curosurf, Infasurf, and Survanta are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending one or more liposome carriers with one or more pharmaceutically acceptable carriers. Optionally, additional active agents may be incorporated into the mixture as discussed below. The mixture is then formed into particles suitable for pulmonary administration using techniques known in the art, such as lyophilization, spray drying, agglomeration, spray coating, coacervation, low temperature casting, milling (e.g., air-attrition milling (jet milling), ball milling), high pressure homogenization, and/or supercritical fluid crystallization.

An appropriate method of particle formation can be selected based on the desired particle size, particle size distribution, and particle morphology desired for the formulation. In some cases, the method of particle formation is selected so as to produce a population of particles with the desired particle size, particle size distribution for pulmonary administration. Alternatively, the method of particle formation can produce a population of particles from which a population of particles with the desired particle size, particle size distribution for pulmonary administration is isolated, for example by sieving.

It is known in the art that particle morphology affects the depth of penetration of a particle into the lung. Accordingly, dry powder formulations is processed into particles having the appropriate mass median aerodynamic diameter (MMAD), tap density, and surface roughness to achieve delivery of the one or more active agents to the desired region(s) of the lung. For example, preferred particle morphologies for delivery to the deep lung are known in the art, and are described, for example, in U.S. Pat. No. 7,052,678 to Vanbever, et al.

Particles having a mass median aerodynamic diameter (MMAD) of greater than about 5 microns generally do not reach the lung; instead, they tend to impact the back of the throat and are swallowed. Particles having diameters of about 3 to about 5 microns are small enough to reach the upper- to mid-pulmonary region (conducting airways), but may be too large to reach the alveoli. Smaller particles, (i.e., about 0.5 to about 3 microns), are capable of efficiently reaching the alveolar region. Particles having diameters smaller than about 0.5 microns can also be deposited in the alveolar region by sedimentation.

The precise particle size range effective to achieve delivery to the alveolar region will depend on several factors, including the tap density of particles being delivered. Generally speaking, as tap density decreases, the MMAD of particles capable of efficiently reaching the alveolar region of the lungs increases. Therefore, in cases of particles with low tap densities, particles having diameters of about 3 to about 5 microns, about 5 to about 7 microns, or about 7 to about 9.5 microns can be efficiently delivered to the lungs. The preferred aerodynamic diameter for maximum deposition within the lungs can be calculated. See, for example, U.S. Pat. No. 7,052,678 to Vanbever, et al.

Microparticles cannot diffuse through mucus even if their surface is muco-resistant. However, mucus-penetrating particles can be encapsulated in microparticles to impact upper lung, and subsequently release the liposomes. In some cases, the particles are spherical or ovoid in shape. The particles can have a smooth or rough surface texture. The particles may also be coated with a polymer or other suitable material to control release of one or more active agents in the lungs.

Dry powder formulations can be administered as dry powder using suitable methods known in the art. Alternatively, the dry powder formulations can be suspended in the liquid formulations described below, and administered to the lung using methods known in the art for the delivery of liquid formulations.

2. Liquid Formulations

Liquid formulations contain one or more liposome carriers suspended in a liquid pharmaceutical carrier. Suitable liquid carriers include, but are not limited to water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human, which is adjusted to the desired hypotonicity.

Preferably, liquid formulations are isotonic relative to physiological fluids and of approximately the same pH, ranging e.g., from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

In some cases the liquid formulation may contain one or more solvents that are low toxicity organic (i.e. nonaqueous) class 3 residual solvents, such as ethanol, acetone, ethyl acetate, tetrahydrofuran, ethyl ether, and propanol. These solvents can be selected based on their ability to readily aerosolize the formulation. Any such solvent included in the liquid formulation should not detrimentally react with the one or more active agents present in the liquid formulation. The solvent should be sufficiently volatile to enable formation of an aerosol of the solution or suspension. Additional solvents or aerosolizing agents, such as a freon, alcohol, glycol, polyglycol, or fatty acid, can also be included in the liquid formulation as desired to increase the volatility and/or alter the aerosolizing behavior of the solution or suspension.

Liquid formulations may also contain minor amounts of polymers, surfactants, or other excipients well known to those of the art. In this context, "minor amounts" means no excipients are present that might adversely affect uptake of the one or more active agents in the lungs.

3. Aerosol Formulations

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment.

In some cases, a device is used to administer the formulations to the lungs. Suitable devices include, but are not limited to, dry powder inhalers, pressurized metered dose inhalers, nebulizers, and electrohydrodynamic aerosol devices. Inhalation can occur through the nose and/or the mouth of the patient. Administration can occur by self-administration of the formulation while inhaling or by administration of the formulation via a respirator to a patient on a respirator.

B. Topical and Ophthalmic Formulations

Topical or enteral formulations can be prepared as aqueous compositions using techniques is known in the art. Typically, such compositions can be prepared as solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, emulsomes, sprays, gels, creams or ointments.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include agents, for example, sugars or sodium chloride, to adjust the tonicity.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for administration upon reconstitution. Suitable buffers include, but are not limited to, phosphate buffers, acetate buffers, and citrate buffers.

Water soluble polymers are often used in pharmaceutical formulations. Suitable water-soluble polymers include, but are not limited to, polyvinylpyrrolidone, dextran, carboxymethylcellulose, and polyethylene glycol.

Sterile solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for ocular administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution, which are then adjusted to the desired hypotonicity. The formulation may also be a sterile solution, suspension, or emulsion in a nontoxic, parenterally acceptable diluent or solvent such as 1,3-butanediol.

In some instances, the formulation is distributed or packaged in a liquid or semi-solid form such as a solution (eye drops), suspension, gel, cream or ointment. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers. Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known in the art, such as dispersing agents, wetting agents, and suspending agents.

In still other embodiments, the liposomes are formulated for topical administration to mucosa. Suitable dosage forms for topical administration include creams, ointments, salves, sprays, gels, lotions, and emulsions. The compositions may contain one or more chemical penetration enhancers, membrane permeability agents, membrane transport agents, emollients, surfactants, stabilizers, and combination thereof.

In some embodiments, the liposomes can be administered as a liquid formulation, such as a solution or suspension, a semi-solid formulation, such as a gel, a lotion or an ointment, or a solid formulation. A "gel" is a colloid in which the dispersed phase has combined with the continuous phase to produce a semisolid material, such as jelly.

In some embodiments, the liposomes are formulated as liquids, including solutions and suspensions, such as eye drops or as a semi-solid formulation, such as ointment or lotion for topical application to mucosa, such as the eye or vaginally or rectally.

The formulation may contain one or more excipients, such as emollients, surfactants, and emulsifiers.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) that contain drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or liposomes. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alkylene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant or gas-emitting component.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7.

D. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Formulations may be prepared using one or more pharmaceutically acceptable excipients, including diluents, preservatives, binders, lubricants, disintegrators, swelling agents, fillers, stabilizers, and combinations thereof.

Excipients, including plasticizers, pigments, colorants, stabilizing agents, and glidants, may also be used to form coated compositions for enteral administration. Delayed release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules.

The liposomes may be coated, for example to delay release once the particles have passed through the acidic environment of the stomach. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions that include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

IV. Methods of Use

The particles described herein can be used to deliver one or more therapeutic, prophylactic, and/or diagnostic agents. The agents can be encapsulated in, associated (e.g., covalently or non-covalently) with the surface, or, and/or dispersed within the particles. The particles can be modified to contain one or more targeting moieties for targeted drug delivery. The particles can be modified prior to particle formation, e.g., the material used to form the particles is modified prior to particles formation, or after the particle is formed. The particles can be formulated for controlled release of the agent, such as by selection of the materials used to form the particles and/or coating the particles with one or more controlled release coatings. The particles can also be coated to vary the surface properties, e.g., charge, of the particles, for example, to reduce surface charge and make them more neutral.

Cardiovascular Disease

High-density lipoprotein (HDL) is a natural nanoparticle that transports peripheral cholesterol to the liver. Reconstituted high density lipoprotein (rHDL) exhibits anti-atherothrombotic properties and is being considered as a natural treatment for cardiovascular diseases. Furthermore, HDL nanoparticle platforms have been created for targeted delivery of therapeutic and diagnostic agents. The current methods for HDL reconstitution involve lengthy procedures that are challenging to scale up. A central need in the synthesis of reconstituted HDL, and multifunctional nanomaterials in general, is to establish large-scale production of reproducible and homogeneous batches in a simple and efficient fashion.

Atherosclerosis is a progressive disease in which the accumulation of cholesterol and inflammatory cells in vessel wall of arteries can eventually lead to myocardial infarction or stroke. High levels of serum low-density lipoprotein (LDL) increase the progression of atherosclerosis and the risk of coronary artery disease (CAD). On the other hand, high-density lipoprotein (HDL) exhibits athero-protective properties and therefore high levels are linked to a decreased risk of CAD. This is due to HDL's ability to remove and transport cholesterol from atherosclerotic plaques to the liver via a process known as reverse cholesterol transport (RCT). Traditional anti-atherosclerotic therapies, such as statins, lower LDL levels systemically, but elevating HDL levels are believed to hold great promise. Amongst different approaches, including the application of cholesteryl ester transfer protein (CETP) inhibitors, direct infusion of reconstituted HDL is an emerging treatment for cardiovascular disease. For example, HDL infusions have been reported to modulate fatty acid metabolism and support cholesterol efflux, which has been shown to reduce arterial cholesterol and myocardial lesions in a rat model and human atherosclerotic plaque.

Moreover, HDL's endogenous character makes it well suited as a vehicle for targeted delivery of diagnostic and therapeutic agents. For example, HDL nanoparticles have been reconstituted to carry inorganic nanocrystals as contrast agents for medical imaging as well as to serve as delivery vehicles for siRNAs or drugs. The reconstitution of such HDL nanoparticles involves multi-step processes, which are highly dependent on synthetic conditions, are difficult to scale up, and are laborious. For example, the cholate, sonication, and vesicle insertion methods are time consuming, requiring at least 24 hours to perform[3]. A central challenge in the synthesis of therapeutic and diagnostic HDL-based nanomaterials is to establish large-scale and continuous production methods with high reproducibility, yield, and homogeneity, while simultaneously reducing the number of preparation steps.

The microfluidic methodologies described herein have been used for the high-throughput, single-step synthesis of HDL-mimicking nanomaterials (referred to as µHDL) that can also contain hydrophobic molecules for drug delivery, such as simvastatin, and fluorophores, or inorganic nanocrystal cores of gold, iron oxides, and quantum dots to enable its detection by computed tomography (CT), magnetic resonance imaging (MRI), or fluorescent microscopy, respectively The physicochemical properties of µHDL can be readily varied and optimized by manipulating mixing speeds and the lipid to protein ratios. µHDL prepared by the methods described herein has similar morphological and compositional properties to native HDL and conventionally reconstituted rHDL. The biological properties of µHDL were validated by studying its interaction with macrophages, and comparing cholesterol efflux capacity with native HDL.

V. Device

The methods described herein use a device which allows for the simultaneous formation of at least symmetrical microvortices when the solutions are mixed together. The device is configured such that the ratio of the fluid flow rate in the central fluid inlet channel to the combined fluid flow rate in the two outer fluid inlet channels is between about 1:10 and about 1:30, preferably between about 1:10 and about 1:20.

The microvortices can be generated at higher Reynolds numbers than described in the prior art. In some embodiments, the Reynolds number is greater than about 30, such as about 30 to about 150, preferably about 30 to about 100. In some embodiments, the Reynolds number is about 30, 40, 45, 55, 60, 65, 70, 75, 80, 85, 90, 95, or 100.

The microfluidic system may contain any number of inlets, such as at least 2, 3, 4, 5, 6, 7, 8, 9, 10, or more inlet streams. The flow of each inlet stream is regulated by a source of fluid, wherein the application of pressure to the source causes the flow of fluid in the inlet stream.

In general, a microfluidic device contains at least two channels that converge into a mixing apparatus, and the channels join together at an angle ranging between zero degrees and 180 degrees. In some embodiments, the channels join together at an angle of approximately 10 degrees, approximately 20 degrees, approximately 30 degrees, approximately 40 degrees, approximately 50 degrees, approximately 60 degrees, approximately 70 degrees, approximately 80 degrees, approximately 90 degrees, approximately 100 degrees, approximately 110 degrees, approximately 120 degrees, approximately 130 degrees, approximately 140 degrees, approximately 150 degrees, approximately 160 degrees, or approximately 170 degrees. A stream of fluid is capable of flowing through each channel, and the streams join and flow into the mixing apparatus. Typically, inventive microfluidic devices contain an outlet channel from the mixing apparatus.

In some embodiments, the device contains at least 3, preferably 3, inlets which are parallel and/or perpendicular to each other. In specific embodiments, the inlets converge to form a mixing chamber, which is a portion of the device distinct from the inlets.

In some embodiments, the channels and/or mixing apparatus have a circular cross-section. In some embodiments, the channels and/or mixing apparatus have an oval or ovaloid cross-section. In some embodiments, the channels and/or mixing apparatus have an elliptical or an ellipsoid cross-section. In some embodiments, the channels and/or mixing apparatus have a cross-section of irregular shape. In some embodiments, the channels that converge into the mixing apparatus are of uniform shape. In some embodiments, the channels that converge into the mixing apparatus are not of uniform shape.

In some embodiments, the device is characterized by having one or more of the following features:
 (a) the height of the fluid inlet channels is greater than the width of the fluid inlet channels,
 (b) the distance between adjacent fluid inlet channels is greater than the width of the fluid inlet channels,
 (c) the width of the mixing channel is at least six times the width of the fluid inlet channels,
 (d) the height of the mixing channel is more than 1.5 times the width of the fluid inlet channels, and
 (e) the length of the mixing channel is at least two times the width of the mixing channel In some embodiments, the width of the fluid inlet channels is between about 10 and about 500 microns, preferably about 200 microns.

In some embodiments, the height of the fluid inlet channels is between about 20 and about 1000 microns, preferably about 400 microns.

In some embodiments, the width of the mixing channel is greater than 100 microns, preferably greater than 1000 microns, more preferably greater than about 2000 microns.

In some embodiments, the length of the mixing channel is greater than about 10 millimeters, preferably greater than 15 millimeters, more preferably greater than 20 millimeters.

The channels/inlets may be formed of any material suitable for the flow of fluid through the channels. Typically, the material is one that is resistant to solvents and non-solvents that are used in the preparation of particles. In general, the material is not one that will dissolve or react with the solvent or non-solvent. In some embodiments, channels are composed of glass, silicon, metal, metal alloys, polymers, plastics, photocurable epoxy, ceramics, or combinations thereof. In some embodiments, a channel and/or mixing apparatus is composed of a metal and/or metal alloys (e.g. iron, titanium, aluminum, gold, platinum, chromium, molybdenum, zirconium, silver, niobium, alloys thereof, etc.). In some embodiments, a channel and/or mixing apparatus is composed of a polymer and/or plastic, including, but not limited to, polycarbonate, polyethylene terephthalate (PET) polyethylene terephthalic ester (PETE), polytetrafluoroethylene (PTFE), polydimethylsiloxane (PDMS), polyurethane, bakelite, polyester, etc. In some embodiments, channels are composed of photocurable epoxy. In some embodiments, a channel and/or mixing apparatus is composed of polydimethylsiloxane. In some embodiments, a channel and/or mixing apparatus is composed of ceramics (e.g. silicon nitride, silicon carbide, titania, alumina, silica, etc.).

In some embodiments, channels are formed by lithography, etching, embossing, or molding of a polymeric surface. In general, the fabrication process may involve one or more of any of the processes described herein, and different parts of a device may be fabricated using different methods and assembled or bonded together.

Typically, a source of fluid is attached to each channel, and the application of pressure to the source causes the flow of the fluid in the channel. The pressure may be applied by a syringe, a pump, and/or gravity. In some embodiments, the applied pressure is regulated (i.e. the applied pressure may be increased, decreased, or held constant). In some embodiments, the flow rate is regulated by adjusting the applied pressure. In some embodiments, the flow rate is regulated by adjusting the size (e.g. length, width, and/or height) of the channel. In some embodiments, the flow rate may range from 0.001 µl/min to 1.0 ml/min.

In some embodiments, the same amount of pressure is applied to all of the channels and/or inlet streams. In some embodiments, different amounts of pressure are applied to different channels and/or inlet streams. Thus, in some embodiments, the flow rate may be the same through all channels and/or inlet streams, or the flow rate may be different in different channels and/or inlet streams.

In some embodiments, inventive microfluidic devices may optionally contain an apparatus for controlling temperature. In certain embodiments, the particles are prepared in the microfluidic device at approximately room temperature. In certain embodiments, the particles are prepared in the microfluidic device at a temperature ranging from approximately 0° C. to approximately 10° C. In certain embodiments, the particles are prepared in the microfluidic device at a temperature ranging from approximately 10° C. to approximately 20° C. In certain embodiments, the particles are prepared in the microfluidic device at a temperature ranging from approximately 20° C. to approximately 30° C. In certain embodiments, the particles are prepared in the microfluidic device at a temperature ranging from approximately 30° C. to approximately 40° C.

EXAMPLES

Material and Methods

Microfluidic Device Design and Fabrication

The microfluidic device had three inlet channels with rectangular cross-sections of dimensions 200 µm wide, 400 µm high, and 10 mm long. These inlet channels converged to form a single outlet channel of rectangular cross-section with dimensions 2000 µm wide, 400 µm high, and 20 mm long. The device was fabricated with polydimethylsiloxane (PDMS) (SYLGARD 184, Dow Corning, Midland, Mich.) using standard soft-lithography techniques. Briefly, Fabrication of master molds was performed by patterning a thin layer of negative SU-8 photoresist (MicroChem Corp., Newton, Mass.) on a silicon wafer. After exposure to UV light and chemical developing, this wafer was used as the mold to create the PDMS microchannels. The PDMS and the glass were strengthened by first treating both surfaces with oxygen plasma before adhesion. This increased the hydrophilicity of the surfaces so that the PDMS and glass would bond covalently.

Particle Sizing

Nanoparticle size was analyzed three times for each sample using dynamic light scattering (DLS) with Zeta-PALS (Brookhaven Instruments Corporation, US). The nanoparticle samples of 100 µL were gently suspended and mixed into 200 µL PBS in a disposable low-volume cuvette. All measurements were performed after diluting the solvent (i.e. acetonitrile) to ensure that any size variation observed in the results was not due to the effect of the remaining solvent. Dilution of the solvent was performed by three-time centrifugal purification processes of the solution with purified water.

Particle Visualization

Nanoparticles were imaged by transmission electron microscopy (TEM; JEOL JEM-299CX) at an acceleration voltage of 200 kV. Samples were prepared by depositing 10 µL of the nanoparticle suspension onto 200-mesh carbon-coated copper grid. The samples were blotted away for 15 minutes and the grids were negatively stained for 2 minutes with filtered 2% uranyl acetate aqueous solution. The grids were then washed with double-distilled water and air-dried prior to imaging.

Reynolds Number and Flow Rate

Three glass syringes were mounted on syringe pumps (NE-1010-U, Kats Scientific) to regulate flow rates through the device. The flow rates in the outer streams of the lipid and lipid-PEG in water were varied from 10 µL/min to 10 mL/min while the flow rate in the central stream of the PLGA in acetonitrile was varied from 2 µL/min to 2 mL/min. Reynolds number (Re) was calculated using the following equation.

$$Re = \frac{\rho U D_h}{\mu} = \frac{\rho U}{\mu} \frac{2wh}{w+h} = \frac{\rho}{\mu} \frac{2Q}{w+h}$$

where Q is the flow rate; µ represents the fluid's viscosity; w and h represent the channel width (2000 µm) and height (400 µm); ρ represents the fluid's density; U represents the fluid's average velocity.

Flow Visualization and Microscopy

Flow patterns were visualized using a stereo microscope (Leica M125, Leica Microsystems, Bannockburn Ill.). The central stream has a 10:1 ratio of deionized water and black ink and the other outer streams have deionized water. Images were taken at Reynolds numbers of 30, 75, and 150 for polymer-lipid hybrid nanoparticles and 150 for lipid nanoparticles.

For the lipid nanoparticles, three glass syringes were mounted on syringe pumps (NE-1010-U, Kats Scientific) to regulate flow rates through the device. The flow rate in the outer streams of apoA-I in PBS was set to 5 mL/min (total 10 mL/min for both) while the flow rate in the central stream of the lipids was 1 mL/min Reynolds number (Re) was calculated using the following equation:

$$Re = \frac{\rho U D_h}{\mu} = \frac{\rho U}{\mu} \frac{2wh}{w+h} = \frac{\rho}{\mu} \frac{2Q}{w+h}$$

where Q is the flow rate; $\mu$ represents the fluid's viscosity; w and h represent the channel width (2000 µm) and height (400 µm); $\rho$ represents the fluid's density; U represents the fluid's average velocity. The flow rates and the resulting Reynolds numbers were shown.

Numerical Simulations

Numerical simulations of the flow field were conducted using the commercial CFD solver (SC/Tetra, CRADLE, Beavercreek, Ohio) in order to solve the non-linear Navier-Stokes equations governing the conservation of mass and momentum within the fluid elements. Advection-diffusion equations were also solved to predict the flow field and the user-defined scalar species. The diffusion coefficients for the scalar species used in the simulations were assumed to be 1e-10 m2/s corresponding to that of water at approximately room temperature3. We assumed a Newtonian fluid having the properties of water at room temperature and no-slip boundary conditions on all the walls. Mesh independence was verified by examining higher density meshes. Flow rates were specified at the three inlets. Convergence limits were set so that velocities converged within 0.1% and mass fractions for the central stream species reached their asymptotic values within 0.01%.

Dynamic Light Scattering

The nanoparticle samples were suspended in deionized water and nanoparticle size was analyzed a minimum of three times for each sample by dynamic light scattering (DLS) using a ZetaPALS system (Brookhaven Instruments Corporation, US).

Cholesterol Efflux Assay

In cholesterol efflux study, macrophages were loaded with [1.2-3]-Cholesterol then incubated with HDL solutions. The cholesterol efflux was measured by scintillation.

CT Scanning

Particle solutions and cell pellets were imaged on 256-slice Brilliance iCT scanner (Philips Medical Systems Nederland B.V., The Netherlands). Gold attenuation value (expressed in Hounsfield (HU) units) were obtained from 3 selected regions of interest and converted to Au concentration using predetermined formula. The CT images were obtained using the Osirix software.

FeO-µHDL Incubation with Macrophages 500 000 cells were seeded per well in 6 well plates and let to adhere overnight. The cells were then incubated with 2 mL of media containing FeO nanoparticles at a concentration of Fe 40 µg/mL for 7 hours (2 wells per condition). The cells were then washed 3 times in PBS, collected using scrappers and centrifuged at 500 g for 5 minutes. Cells were dispersed in 4% PFA and finally allowed to form a pellet.

MRI Imaging

Cell pellets were scanned using a 7T MRI system (Bruker Instruments) using a gradient echo sequence: echo time: 2 ms, repetition time: 2000 ms, field of view: 20×20×10 mm, imaging matrix 128×128×16, flip angle: 3 degrees. The images were then obtained using the Osirix software.

Example 1. Synthesis of Lipid-Polymer Hybrid Nanoparticles

Lecithin (soybean, refined, molecular weight ~330 Da; Alfa Aesar, Ward Hill, Mass.) and DSPE-PEG (1,2-distearoyl-sn-glycero-3-phosphoethanolamine-N-carboxy (polyethylene glycol); molecular weight ~2850 Da; Avanti Polar Lipids, Alabaster, Ala.) were dissolved in 4 wt % aqueous ethanol solution and introduced into the outer channels of the microfluidic device. The mole ratio of lecithin to DPSE-PEG was 7:3. PLGA (poly(lactide-co-glycolide); inherent viscosity of 0.55~0.75; Lactel, Pelham, A L) was dissolved in acetonitrile. The final concentrations of the PLGA and lipid solutions were achieved by preparing aliquots (PLGA solution (15 mg/mL) and lipid solution (1.5 mg/mL)) and diluting them to the PLGA-to-lipid ratios used in the experiments.

A schematic of a single-layer, three-inlet microfluidic platform generating two symmetric microvortices and a 3D focusing pattern is shown in FIG. 1a. A cross sectional view of the device is shown in FIG. 1b. FIG. 1c is an illustrative structure of LPH nanoparticles synthesized in the microfluidic platform. FIG. 1d is a graph showing that productivity of PLGA-PEG particle synthesis as a function of the method of synthesis. FIG. 1e is a graph showing the average distribution of the nanoparticles produced through the controlled microvortices. The average sizes are 55 nm (Re=150) and 81 nm (Re=75). The Reynolds number was computed by the microfluidic dimensions and flow rate used in the experiment. FIGS. 1 $f$ and $g$ are transmission electron microscopy (TEM) images that demonstrate the synthesized nanoparticles with two distinct sizes for Re=150 (f) and Re=75 (g) with only changes of flow rates (i.e. Reynolds number (Re)). The scale bars are both 100 nm.

The concentrations of the various reactants used to form the particles are shown in Table 2.

TABLE 2

| | | | Concentrations of reactants | | | | |
|---|---|---|---|---|---|---|---|
| PLGA/ lipid (wt) | PLGA (mg) | Acetonitrile (mL) | PLGA solution (mg/mL) | Lecithin (mg) | DSPE-PEG (mg) | 4% ethanol Aq. (mL) | lipid solution (mg/mL) |
| 5 | 3.750 | 10 | 0.375 | 0.32 | 1.18 | 20 | 0.075 |
| 10 | 7.500 | 10 | 0.750 | 0.32 | 1.18 | 20 | 0.075 |
| 25 | 18.75 | 10 | 1.875 | 0.32 | 1.18 | 20 | 0.075 |

TABLE 2-continued

| | | | Concentrations of reactants | | | | |
|---|---|---|---|---|---|---|---|
| PLGA/ lipid (wt) | PLGA (mg) | Acetonitrile (mL) | PLGA solution (mg/mL) | Lecithin (mg) | DSPE-PEG (mg) | 4% ethanol Aq. (mL) | lipid solution (mg/mL) |
| 50 | 37.50 | 10 | 3.750 | 0.32 | 1.18 | 20 | 0.075 |
| 100 | 75.00 | 10 | 7.500 | 0.32 | 1.18 | 20 | 0.075 |

The flow rates and the resulting Reynolds numbers are shown in Table 3 and FIG. 2.

TABLE 3

| Reynolds Number as a function of flow rate | | | | |
|---|---|---|---|---|
| Reynolds number | Flow rates (mL/min) | | | |
| (Re) | Lipid (L) | PLGA (C) | Lipid (R) | Total |
| 0.3 | 0.01 | 0.002 | 0.01 | 0.022 |
| 30 | 1.0 | 0.2 | 1.0 | 2.2 |
| 75 | 2.5 | 0.5 | 2.5 | 5.5 |
| 150 | 5.0 | 1.0 | 5.0 | 11.0 |
| 300 | 10.0 | 2.0 | 10.0 | 22.0 |

Figure 3:
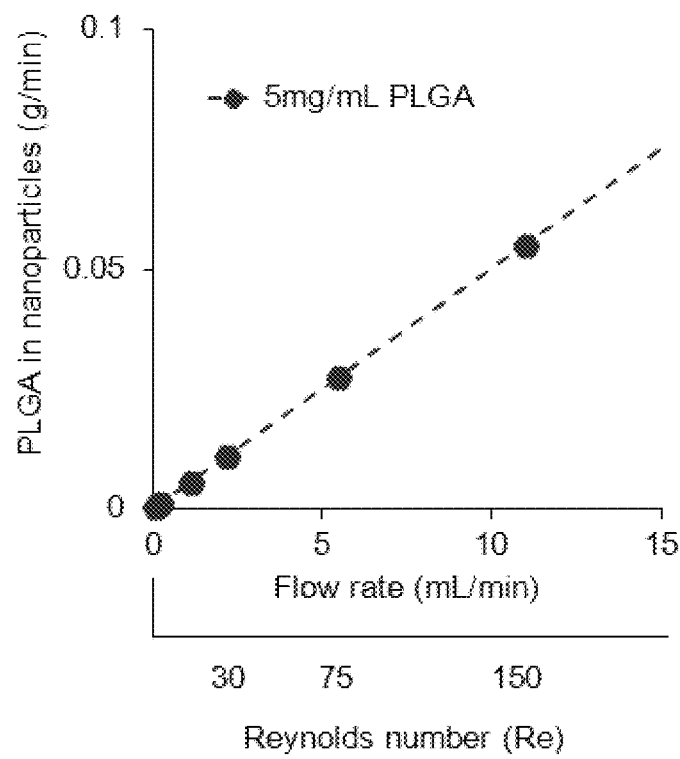
FIG. 3 is a graph showing the amount of PLGA in the nanoparticles as a function of flow rate and Reynolds number.

FIG. 3 is a graph showing the amount of PLGA in the nanoparticles as a function of flow rate and Reynolds number.

It has been shown that an increase in PLGA-to-lipid weight ratios leads to an increase in nanoparticle size using bulk synthesis methods. The methods described herein were used to investigate nanoparticle size as a function Reynolds number (e.g., 30, 75, and 150) while maintaining constant PLGA-to-lipid weight ratios of 5, 10, 25, 50, and 100 (FIG. 4a and Table 43 below).

TABLE 4

| PLGA(wt)/ | Reynolds number (Re) | | |
|---|---|---|---|
| Lipid(wt) | 30 | 75 | 150 |
| 5 | 82 | 32 | 25 |
| 10 | 93 | 81 | 55 |
| 25 | 107 | 85 | 62 |
| 50 | 124 | 95 | 79 |
| 100 | 174 | 99 | 87 |

Figure 5:
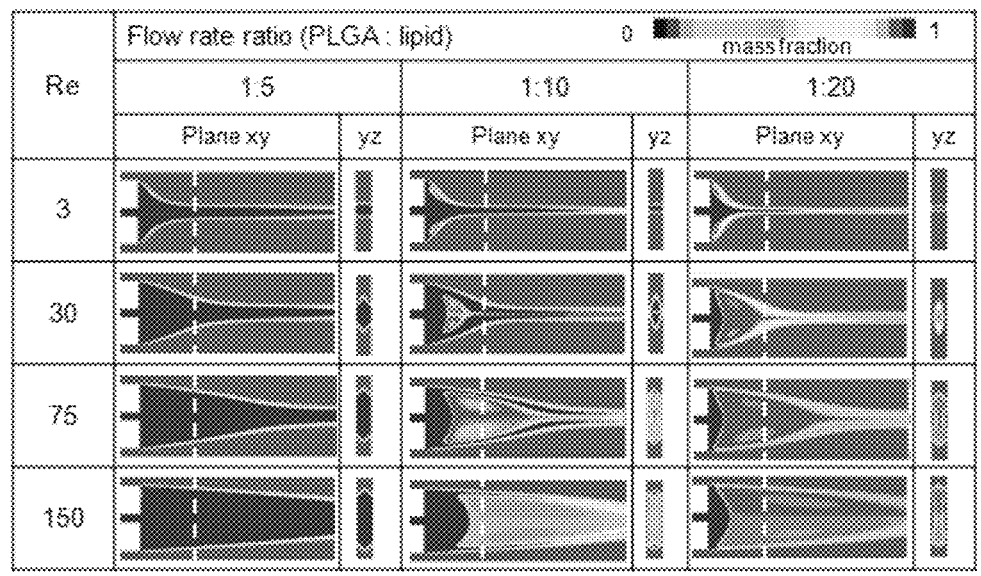
FIG. 5 is a computational fluid dynamics simulation showing microvortex patterns with variations of flow rate ratios of polymer to lipid streams and Reynolds numbers.
Figure 6A:
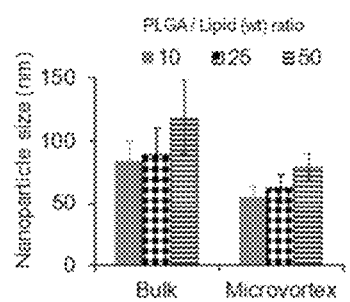
FIG. 6a is a graph showing nanoparticle size at different PLGA/lipid ratios prepared by bulk and microvortices.

Desired flow patterns were simulated and predicted using computational fluid dynamics (CFD) and visualized with a stereo-microscope, which demonstrated controlled microvortex patterns at Re=30, 75, 150 (FIGS. 4b, 4c, and 5). It was observed that an increase in the Reynolds number resulted in a decrease in the nanoparticle size at the given PLGA-lipid ratio. For example, the variation of the Reynolds number from 30 to 150 with a PLGA-to-lipid ratio of 10 resulted in a size decrease from 93 to 55 nm (FIG. 6a and Table 4). This illustrated that by varying flow rates in the microvortex platform the nanoparticle size could be reliably controlled, while keeping the same PLGA-lipid composition. It was also observed that this size control is less predictable and controllable at both high and low PLGA-to-lipid ratios (FIG. 6a). A minimal size of 20 nm was achieved at a ratio of 5 with high Reynolds numbers (Re=75 or 150). Increasing the PLGA-to-lipid ratio to 100 resulted in an increased nonlinearly of nanoparticle size at a Reynolds number of 30, where the microvortices are not strong enough to mix the excessive polymer with lipid efficiently. This size map indicated that varying these two parameters could produce the nanoparticles in a size range of 30 to 170 nm.

Figure 6B:
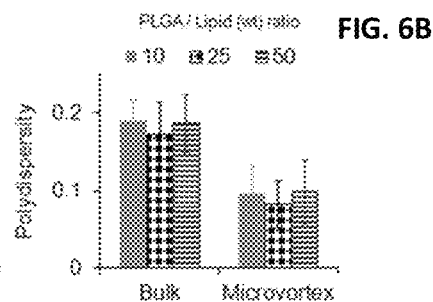
FIG. 6b is a graph showing the polydispersity of the average distribution. The error bars are both standard deviations of different batches.
Figure 6C:
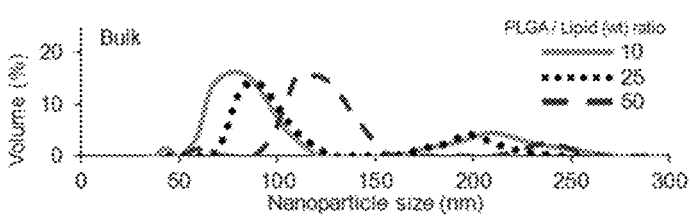
FIGS. 6c and 6d show the nanoparticle size distributions for bulk (c) and microvortices (d). The solid, dotted, and dashed lines represent the PLGA-to-lipid weight ratios of 10, 25, and 50, respectively.

Simulation of the flow patterns demonstrated that convective mixing between polymer and lipid is not dominant enough for nanoparticle synthesis at lower Reynolds number (Re=3) due to underdeveloped microvortices, whereas the higher Reynolds numbers (Re>30) provide strong and rapid convective mixing. The variation of the nanoparticle size with the patterns of the microvortices was compared (FIGS. 6b and 6c). Underdeveloped microvortex did not completely mix the polymer and lipid at Re=30, which can cause aggregation at higher polymer concentrations, resulting in wide nanoparticle size distributions. In contrast, rapid convective mixing by microvortices (Re=75 or 150) resulted in narrow size distributions. Moreover, it was observed that the size changes were more sensitive to the Reynolds number than the polymer-lipid compositions, indicative of the importance of the mixing speed (i.e. Reynolds number). The abrupt decrease in the size at the polymer-lipid ratio of 5 can be explained by precluded polymer aggregation as a result of excessive lipid, as previously reported. This result illustrates that LPH nanoparticles quickly synthesized in the microvortex platform not only have similar characteristics to those assembled in bulk approaches, but also exhibit similar physicochemical properties, which can be readily controlled with simple flow rate changes, without the need for adjusting polymer and lipid compositions.

Figure 7A:
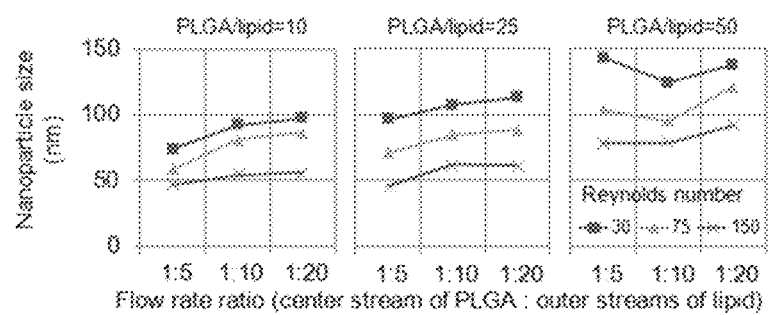
FIG. 7a are graphs showing the effect of flow rate ratios (1:5, 1:10, and 1:20) of [PLGA stream] to [outer lipid streams] on nanoparticle size with respect to Reynolds number (30, 75, and 150) and polymer-lipid compositions (10, 25, and 50).
Figure 7B:
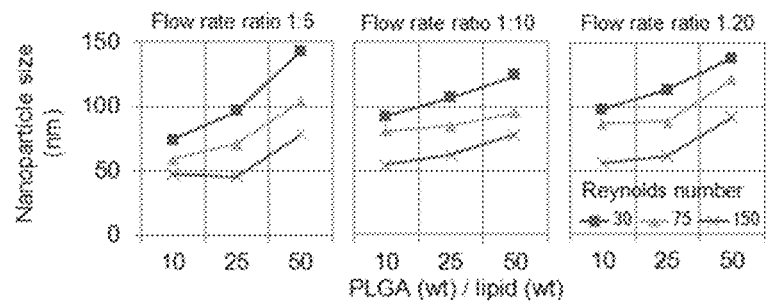
FIG. 7b are graphs showing the effects of polymer-lipid compositions (10, 25, and 50) on nanoparticle size with respect to Reynolds number (30, 75, and 150) and flow rate ratios (1:5, 1:10, and 1:20).
Figure 7C:
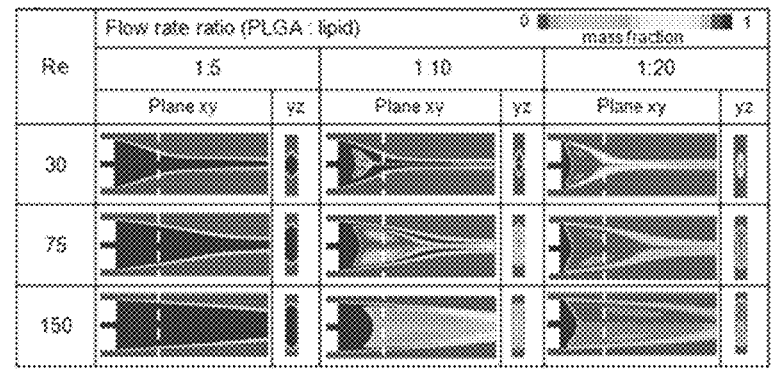
FIG. 7c shows the controllable microvortices in the xy and yz planes. At a flow rate ratio of 1:5, microvortex patterns were not well developed due to relatively higher portion of the central stream in the channel while the vortices were well developed in flow rate ratios of 1:10 and 1:20. Increasing the Reynolds number resulted in clearer microvortex formation while vortex patterns were undeveloped at Re=3.

To gain more insight into the role of microvortex patterns in nanoparticle formation, the flow rate ratios of [PLGA stream] to [outer lipid streams] were varied, while varying the Reynolds number as well (FIG. 7). Changing flow rate ratios from 1:10 to 1:20 did not appear to have a notable effect on the nanoparticle size at PLGA-to-lipid ratios of 10, 25, and 50 (FIG. 7a), indicating that nanoparticle assembly relied on well-developed microvortices. As demonstrated above (FIG. 4), an increase in the PLGA-to-lipid ratio at a constant flow rate ratio led to an increase of nanoparticle size (FIG. 7b) at all the flow rate ratios, but this increase was higher at the flow rate ratio of 1:5 (FIG. 7b) where microvortex patterns were not well developed due to relatively higher portion of the central stream in this microfluidic dimension (FIG. 7c). This high sensitivity of the size to the PLGA-to-lipid ratio was also noted at the low Reynolds number (Re=30) (FIGS. 7a and 7b) where the inertial forces were not strong enough to fully develop the microvortex patterns (FIG. 7c). This resulted in larger nanoparticles, which can be explained, in part, by polymer aggregation and poor diffusive mixing (FIG. 7c). It was found that the optimal range of the flow rate ratios should be between 1:10 and 1:20 for an optimal size-controllable nanoparticle synthesis.

Figure 6D:
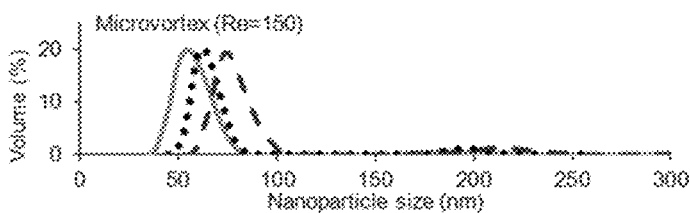

To examine the performance of nanoparticle syntheses by a conventional bulk method and our microvortex approach, the nanoparticle size (FIG. 6a), polydispersity (FIG. 6b), and average size distribution (FIGS. 6c and 6d) using PLGAto-lipid ratios of 10, 25, and 50 were compared. These approaches demonstrated a similar increase in nanoparticle size when the PLGA-lipid ratio was increased (FIG. 6a). However, the synthesis by the conventional bulk method in the same microfluidic device produced larger nanoparticles (80 to 120 nm; see FIGS. 6a and 6c) than those by our microvortex approach (Re=150) (55 to 80 nm; see FIGS. 6a and 6d). The bulk synthesis method resulted in nanoparticle batches that were characterized by a much wider size distribution that had multiple peaks and higher polydispersity (~0.2) (FIGS. 6b and 6c). In contrast, the approach using microvortex-induced rapid mixing resulted in a relatively narrow size distribution that had lower polydispersity (~0.1) (FIGS. 6b and 6d). This monodisperse nanoparticle fraction produced by the microvortex platform represented more than 85% of their overall volume for all PLGA-to-lipid ratios, except at 5 (FIG. 8).

Figure 8:
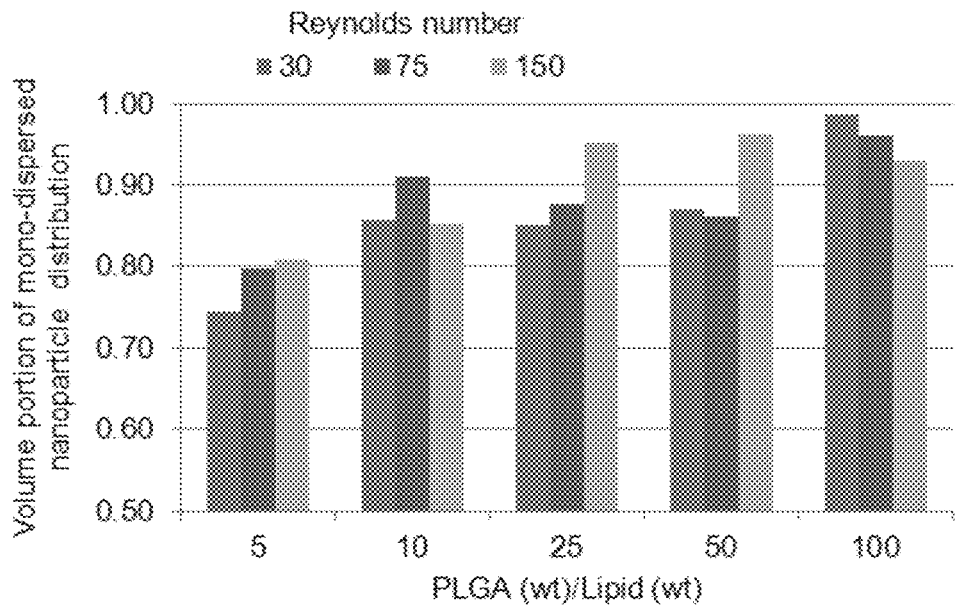
FIG. 8 is a graph showing the volume portion of monodispersed nanoparticle distribution.

Liposomes can also be generated in this microvortex platform, which were easily distinguished by additional peaks around 300~400 nm that usually occupied less than 15% of the overall volume (FIG. 8). This liposome formation caused by the presence of excessive lipid did not significantly affect the size (distribution) of the main PLH nanoparticle formation because convective rapid mixing in the self-assembly of LPH nanoparticles induces uniform lipid and lipid-PEG coverage around polymeric cores.

Figure 9:
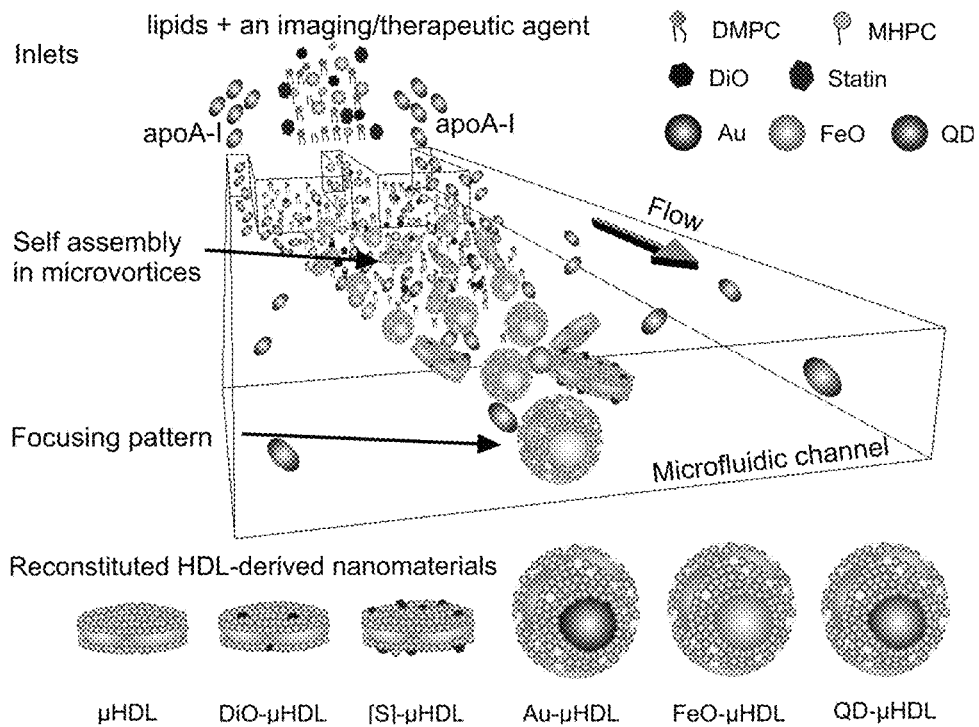
FIG. 9 is a schematic showing the reconstitution of HDL using microfluidics.

The experimental parameters are shown in Table 5. A schematic is show in FIG. 9.

TABLE 5

Experimental parameter for nanoparticle production

| Inlet | Precursor | Solvent | Flow rate mL/min | Re |
|---|---|---|---|---|
| Left | apoA-I (0.2 mg/mL) | PBS | 5 | 152.8 |
| Center | lipids & imaging agents/drugs (see Table 2) | Ethanol, Methanol, Chloroform | 1 | |
| Right | apoA-I (0.2 mg/mL) | PBS | 5 | |

Figure 10:
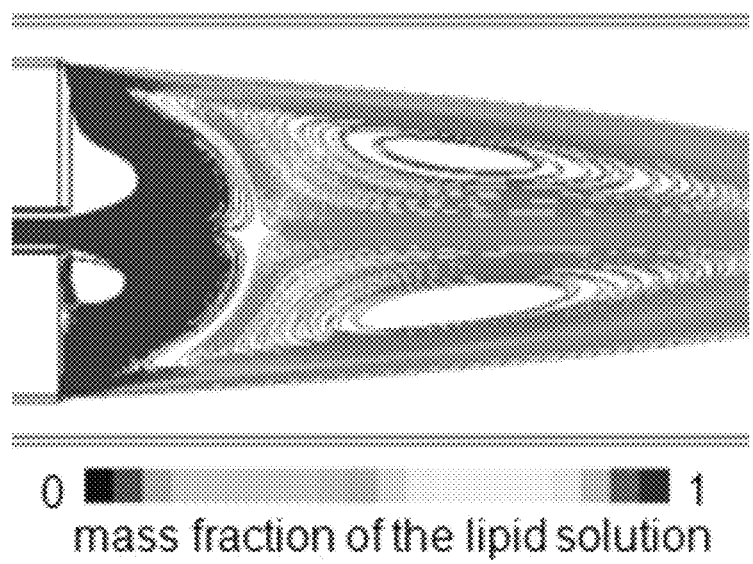
FIG. 10 is a simulation showing dual microvortices at Re=150.

The microfluidic device generated tunable dual microvortices and a focusing pattern at Reynolds number (Re) ~150, thereby allowing for rapid and effective mixing of the solutions in the central inlet and the two outer inlets (FIG. 10). The type or composition of the phospholipids (e.g. DMPC or MHPC) was varied. The conditions for mixing the phospholipid with apoA-I were varied by tuning the microvortex patterns in the microfluidic device. The solvent of the central inlet was determined by the lipophilicity of the individual imaging agent payloads (Table 6).

TABLE 6

| | Lipid/imaging agent | | | Solvent | | |
|---|---|---|---|---|---|---|
| HDL type | DMPC | MHPC | Imaging agent/drug | Ethanol | Methanol | Chloroform |
| μHDL | 10 mg | | | 2 mL | | |
| DiO-μHDL | 10 mg | | DiO: 0.3 mg | 2 mL | | |
| [S]-μHDL | 20 mg | | Simvastatin: 4 mg | 2 mL | | |
| Au-μHDL | 3.5 mg | 1.5 mg | Au: 10 mg | 1.75 mL | 0.05 mL | 0.2 mL |
| FeO-μHDL | | 80 mg | FeO: 5 mg | | 0.2 mL | 1.8 mL |
| QD-μHDL | | 50 mg | QD: 3 nmole | | 0.2 mL | 1.8 mL |

It has been demonstrated that LPH nanoparticles can be produced up to 500 times faster than conventional microfluidic diffusive syntheses. The particle size can be readily controlled with simple changes of flow rates in our microvortex platform, which alters the mixing of polymer and lipid. A desired range of Reynolds numbers (30~150) were predicted that can generate and control microvortices, as well as optimal input ratios of the precursors. As compared to conventional approaches, the method described herein resulted in an improved reproducibility and homogeneity (polydispersity of ~0.1) of the nanoparticle batches. High productivity (3 g/hour) and size control (30~170 nm) are prerequisite for drug nanoparticle formulations to be employed for in vivo applications. Our approach enables the mass production of complex nanoparticle platforms and can facilitate GMP production and clinical translation.

Example 2. Preparation of Multifunctional High-Density Lipoprotein (HDL)-Derived Nanoparticles Multifunctional HDL-mimicking nanomaterials (μHDL, DiO-μHDL, [s]-μHDL, Au-μHDL, FeO-μHDL, and QD-μHDL) were reconstituted using a single-step, self-assembly method in a single layer, 3-inlet microfluidic device.

The self-assembly process in the microfluidic approach occurs due to: (1) the transition of the lipid/payload from an organic solution to an aqueous one, which initiates the formation of lipid aggregates, and (2) the microvortices cause apoA-I to swiftly incorporate in the nascent aggregates, resulting in instantaneous formation of small μHDL nanoparticles. While a typical conventional synthesis typically requires the formation of vesicles via lipid film hydration and subsequent 1 hr sonication and 16 hr incubation with apoA-I, resulting in typical batch sizes of 120 mg of lipids per batch, the HDL production of using the microfluidic approach described herein is continuous at a rate of 420 mg/hr (Tables 5 and 6).

Physicochemical Properties of μHDL

Figure 11A:
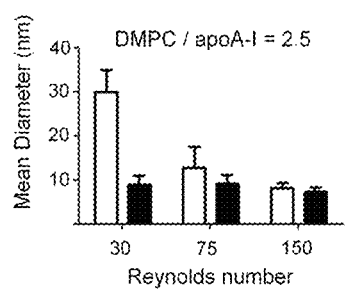
FIG. 11a is a graph showing the size of μHDL as a function of Reynolds number i.e. mixing speed. (DMPC/apoA-I=2.5).

The size of μHDL as a function of the microvortex pattern was determined. By varying the flow rate of each inlet (i.e. Reynolds number), the μHDL diameter could be controlled for a given lipid-to-protein ratio (i.e. DMPC/apoA-I=2.5, FIG. 11a). The average size of μHDL was decreased from 30.0 nm to 8.1 nm by increasing the Reynolds number from approximately 30 to 150. It was noted that the solutions of DMPC and apoA-I were not well mixed due to underdeveloped microvortices at Re~30, whereas they were strongly mixed due to well-developed microvortices at Re ~150 (FIG. 11a). ApoA-I can induce small HDL nanoparticle formation. However, it was found that after simply washing the raw product three times with deionized water, the size was approximately the same across the Reynolds numbers.

Figure 11B:
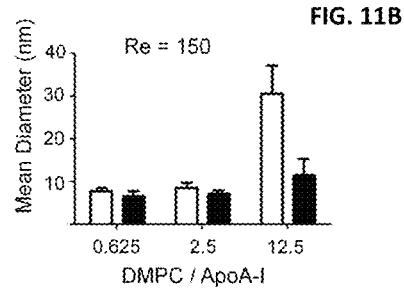
FIG. 11b is a graph showing the size of μHDL with respect to lipid-apoA-I ratio (Re=150).

The change in average size as a function of the DMPC:apoA-I ratio was investigated. The average size of μHDL remained 7.6~8.5 nm as the DMPC:apoA-I ratio increased from 0.625 to 2.5 but increased to approximately 30.6 nm as this ratio increased from 2.5 to 12.5 (FIG. 11b). This increase is also likely due to large lipid aggregates that do not incorporate apoA-I, which were again mostly removed by purification (FIG. 11b). μHDL for these experiments were synthesized with an optimal condition of Re=150.

Figure 11C:
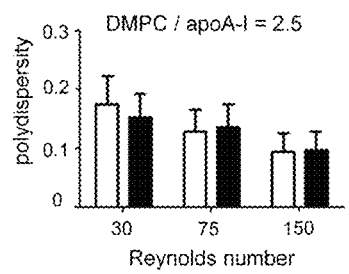
FIG. 11c is a graph showing the polydispersity of μHDL as a function of Reynolds number. (DMPC/apoA-I=2.5).
Figure 11D:
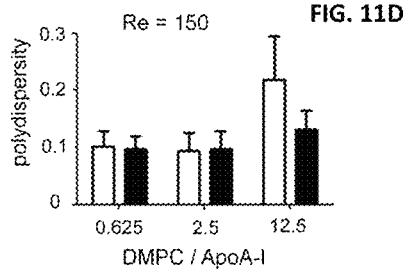
FIG. 11d is a graph showing the polydispersity of μHDL as a function of lipid-apoA-I ratio (Re=150).

The polydispersity of rHDL gradually decreased as the Reynolds number increased, and did not show any significant difference before and after the purification process (FIGS. 11c and 11d). Also, the polydispersity remained 0.094~0.102 but increased up to 0.218 as the DMPC-apoA-I ratio increased. This polydispersity increase is likely due to the formation of lipid aggregates and was found to be reduced after the purification process as well.

The structure of rHDL reconstituted using conventional multi-step methods was compared with that of μHDL, using transmission electron microscopy (TEM). The discoidal shape and characteristic rouleaux structures (stacks of discs on their edge) were observed for both. Dynamic light scattering showed that the average size was not significantly different and was 8-9 nm for both methods, while μHDL had reduced polydispersity compared to the rHDL (FIG. 12B).

Biological Properties of μHDL

In Vitro Experiment

Rhodamine labeled μHDL incubated with murine macrophages to probe nanoparticle uptake (macrophages express several proteins that binds HDL).

Murine sarcoma macrophage cells J774A.1 (ATCC® TIB-67TH, ATCC, USA) were cultured in Dulbecco's Modified Eagle Medium (DMEM) supplemented with 10% Fetal Bovine Serum (FBS, Sigma, USA) and 1% streptomycin/penicillin (corning, USA). Cells were detached, washed in PBS, and counted before the in vitro experiments. Definite number of cells were then seeded and left overnight to adhere.

Macrophages were seeded on microscope chamber slides and allowed to adhere overnight. The cells were then incubated with nanoparticle solutions. After incubation, slides were washed 3 times with PBS and cells were fixed with 4% PFA. Slides were then washed again 3 times with PBS and then mounted with media containing DAPI. Epifluorescence images were taken. Confocal pictures were taken using a Leica TCS SP5 DM confocal using a sequential set-up with QD and DAPI excitation at 405 nm.

In competition-inhibition experiments, macrophages were co-incubated with a fixed concentration of the rhodamine labeled μHDL (21.4 μg/ml ApoA1) and increased amount of native murine HDL extracted from serum. It was observed that the μHDL was taken up by macrophages and that this uptake increased over time (FIG. 13).

Figure 14:
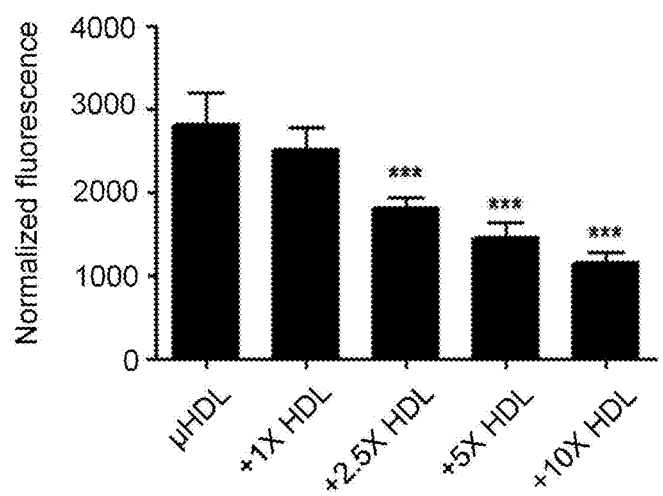
FIG. 14 is a graph of the competition assay showing μHDL uptake by macrophages with respect to increasing concentrations of native HDL extracted from human plasma. Error bar is standard deviation. N=6. *** (P<0.0001).
Figure 15:
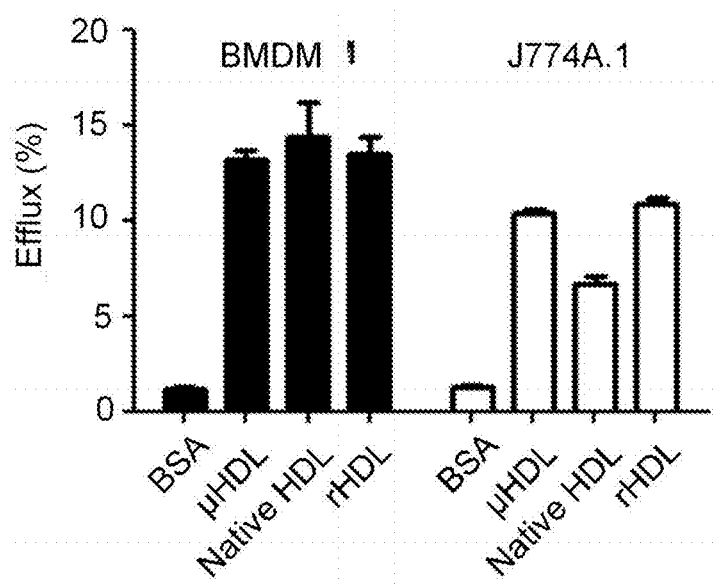
FIG. 15 is a graph showing cholesterol efflux of BSA, μHDL, native HDL, and rHDL (by sonication). Error bar is standard deviation (N=4).

In the competition-inhibition experiment an increased concentration of native HDL led to significant decreases of μHDL uptake in the cells (FIG. 14), indicating that the μHDL was taken up by macrophages through the same pathway as native HDL. The macrophage cholesterol efflux capacity of μHDL was compared with that of native HDL and rHDL. The three HDL types (μ-rHDL, native HDL, and rHDL) produced significant and comparable efflux in both J774A.1 and bone marrow derived macrophages (BMDM) (FIG. 15). These assays demonstrated that μHDL has similar bioactivity to native HDL.

Transmission Electron Microscopy

HDL samples were transferred and washed in an ammonium acetate buffer to remove PBS trace and then negatively stained using an ammonium acetate buffer containing 2% sodium phosphotungstate. Drops of sample solutions were placed onto 100 mesh Formfar coated nickel grids (Electron Microscopy Sciences). Grids were imaged using a Hitachi 7650 microscope connected to a digital camera (Scientific Instruments and Applications) controlled by Maxim CCD software.

Incorporation of Hydrophobic Molecules into μHDL

Using the single-step microfluidic approach, a fluorescent hydrophobic agent (DiO) or an anti-inflammatory hydrophobic drug (simvastatin (S)) was incorporated into μHDL (Table 6).

The mean sizes of DiO-μHDL and [S]-μHDL respectively were 7.3±1.1 and 32±1.3 nm with a polydispersity of less than 0.1. The entrapment efficiencies were 94.2±9.6% for DiO-μHDL and 70.1±7.0% for [S]-μHDL. The uptake of DiO-μHDL in murine macrophages was imaged using confocal microscopy.

Using the same cell line, the biological activity of [S]-μHDL was investigated. Macrophages were seeded in 96 wells plate and allowed to adhere overnight. The cells were then activated for 6 hours with 300 units/mL of interferon-γ and for 16 hours with 300 units/mL of interferon-γ and 25 ng/mL of LPS. The cells were then incubated for 24 hours with FBS free media containing HDL solutions corresponding to 10 μM simvastatin or adequate controls. TNF-α supernatant concentration was measured by ELISA.

Figure 16:
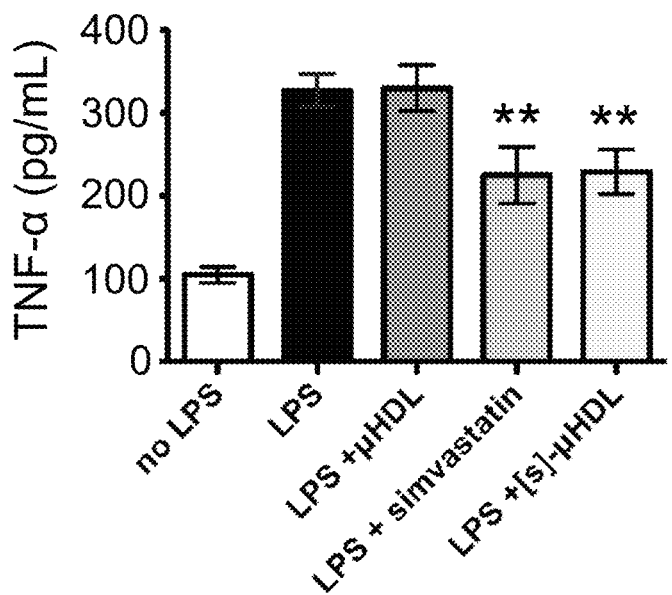
FIG. 16 is a graph showing TNF-α secretion for 24 hr from pre-activated macrophages incubated with [s]-μHDL solution. TNF-α secretion was measured using ELISA. Error bar is standard deviation (N=4). ** (P<0.01).
Figures 17A, 17B, 17C:
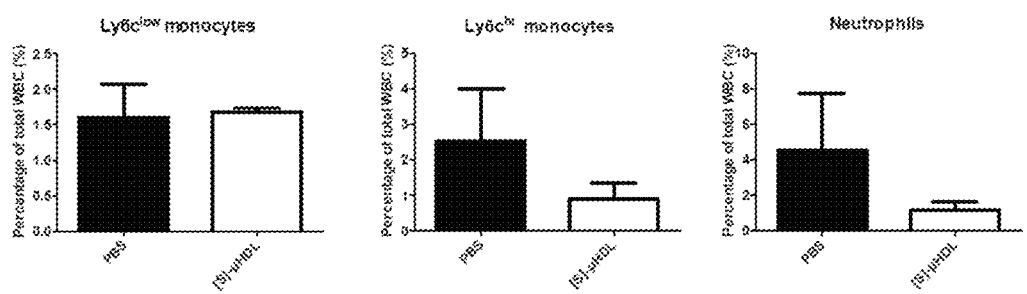
FIGS. 17A-17C are graphs showing the relative percentage of white blood cell (WBC) subsets, Ly6c$^{low}$ monocytes (17A), Ly6c$^{hi}$ monocytes (17B), and neutrophils (17C), after intravenous injection of [s]-μHDL (60 mg/kg simvastatin).

Incubation with [S]-μHDL resulted in a 30% decrease in the secretion of TNF-α, a pro-inflammatory cytokine (FIG. 16). Furthermore, in a pilot experiment in atherosclerotic apolipoprotein-E knockout mice we found neutrophils and inflammatory monocytes (ly6c$^{hi}$) in the total white blood cell subset to be depleted after treatment with [S]-μHDL for a week (FIGS. 17A-C).

Gold Nanocrystal Encapsulated μHDL (Au-μHDL)

Gold nanocrystals were incorporated into the core of μHDL using the microfluidic approach (Table 6). The central stream contained gold nanoparticles mixed with phospholipids dissolved in a solution of ethanol, chloroform, and methanol at a ratio of 35:4:1, while apoA-I in a PBS buffer was infused in the outer channels at a final ratio of apoA-I:lipid ratio of 1:2.5. The resulting solution contained a mixture of Au-μHDL and μHDL having a ratio corresponding to the lipid:gold ratio present in the microfluidic channel Subsequently, Au-μHDL was isolated and purified using a gradient density purification method derived from Havel's ultracentrifugation lipoprotein separation protocol[2].

The uptake of Au-μHDL or Au-PEG (gold nanocrystals shielded by phospholipid-polyethylene glycol) by macrophages in vitro was confirmed by imaging the resultant cell pellets with CT. The contrast in CT images revealed that Au-μHDL was taken up more avidly by the cells compared with the controls. Interestingly, as the gold nanocrystals act as a scaffold for HDL coating, the size of Au-μHDL was not sensitive to changes in the flow rates. Furthermore, Au-μHDL was formed from a variety of phospholipids and their mixtures. The single step microfluidic method not only enabled scale-up production of Au-μHDL but also obviated the need for long incubation steps, heating and extensive purification of prior methods.

FeO and QD Encapsulated μHDL (FeO-μHDL and QD-μHDL)

FeO nanoparticles and quantum dots were co-dissolved with the phospholipids in a solution of chloroform and methanol before being infused to microfluidic channel. While the use of chloroform prevents nanoparticle aggregation in the lipid/nanocrystal solution, the resulting nanoparticles contain residual chloroform which can be removed via evaporation. The nanoparticles are purified by gradient density separation to obtain a homogenous population of single nanocrystal core μHDL. It was observed that the nanoparticle size was correlated to the size of the quantum dots or iron oxide nanocrystals injected in the microfluidic device. Confocal images of macrophages incubated with QD-μHDL revealed its uptake. In addition, magnetic resonance images of macrophages incubated with FeO-PEG and FeO-μHDL (Fe: 40 μg/mL) revealed a hypointense signal that originated from the cell pellets incubated with FeO-μHDL when compared to non-treated cells or cells incubated with FeO-PEG. This signal decay indicated preferential internalization of FeO-μHDL by macrophages.

In Vivo Study

Apolipoprotein-E knockout mice fed with high fat diet for 18 weeks were injected with either PBS or modified [S]-μHDL containing 10% MHPC (60 mg/kg simvastatin per injection) 4 times in a week. 24 hours after the last injection, mice were bled on their right eyes, and white blood cells subset were discriminated using flow cytometry.

We claim:

1. A method of making nanoparticles comprising mixing in a microfluidic device comprising a central fluid inlet channel and two outer fluid inlet channels, wherein the channels converge in a mixing channel prior to the outlet, a solution of one or more materials selected from polymers and lipids with a non-solvent for the one or more materials to form a three-dimensional pattern comprising at least two symmetrical microvortices and focusing the pattern downstream to form the nanoparticles,
   wherein the ratio of the fluid flow rate in the central fluid inlet channel to the combined fluid flow rate in the two outer fluid inlet channels is in a ratio of between about 1:10 and about 1:30, and
   wherein the symmetrical microvortices, generated at a Reynolds number of greater than about 30, produce an effective amount of convective mixing of the solution of one or more materials and the non-solvent to produce a population of the nanoparticles having a homogeneous size distribution.

2. The method of claim 1, wherein the nanoparticles are polymeric nanoparticles.

3. The method of claim 1, wherein the nanoparticles are lipid-polymer hybrid nanoparticles formed by mixing a solution comprising polymer with the non-solvent comprising one or more lipids.

4. The method of claim 1, wherein the non-solvent is an organic solvent.

5. The method of claim 1, wherein the non-solvent is water or an aqueous solvent.

6. The method of claim 3, wherein the non-solvent is water or an aqueous solvent.

7. The method of claim 1, wherein the polymer is a naturally occurring polymer.

8. The method of claim 1, wherein the polymer is a synthetic polymer.

9. The method of claim 7, wherein the polymer is biocompatible.

10. The method of claim 1, wherein the polymer is biodegradable.

11. The method of claim 1, wherein the polymer is selected from the group consisting of polyesters, polyanhydrides, polyalkylene oxides, and copolymers and blends thereof.

12. The method of claim 11, wherein the polymer is polylactide-co-glycolide.

13. The method of claim 7, wherein the polymer comprises a protein.

14. The method of claim 1, wherein the one or more materials are lipids.

15. The method of claim 1, wherein the lipid is a phospholipid.

16. The method of claim 14, wherein the lipid is dissolved in a lower alcohol or an organic solvent.

17. The method of claim 3, wherein the one or more lipids are selected from the group consisting of lecithin, 1,2-distearoyl-sn-glycero-3-phosphoethanolamine-N-[amino (polyethylene glycol)], dimyristoylphosphatidylcholine (DMPC), 1,2-dihexanoyl-sn-glycero-3-phosphocholine (DHPC), 1-myristoyl-2-hydroxy-sn-glycero-phosphocholine (MHPC), and combinations thereof.

18. The method of claim 1, wherein the solution further contains a bioactive agent.

19. The method of claim 18, wherein the bioactive agent is a diagnostic, prophylactic, therapeutic agent, nutriceutical agent, or combinations thereof.

20. The method of claim 18, wherein the bioactive agent is apolipoprotein A-I.

21. The method of claim 1, wherein the nanoparticles further comprise an additional therapeutic or diagnostic agent.

22. The method of claim 21, wherein the additional agent is a cholesterol-lowering agent.

23. The method of claim 1, wherein the nanoparticles are formed at a rate of greater than 0.1 grams of nanoparticles per hour of fluid flow.

24. The method of claim 23, wherein the nanoparticles are formed at a rate of greater than 1.0 grams of nanoparticles per hour of fluid flow.

25. The method of claim 24, wherein the nanoparticles are formed at a rate of greater than 2.0 grams of nanoparticles per hour of fluid flow.

26. The method of claim 25, wherein the nanoparticles are formed at a rate of greater about 3.0 grams of nanoparticles per hour of fluid flow.

27. The method of claim 1, wherein the nanoparticles have an average particle size of between about 5 nm and about 200 nm.

28. The method of claim 1, wherein the fluid flow rate in the central fluid inlet channel to the relative combined fluid flow rate in the two outer fluid inlet channels is between about 1:10 and about 1:20.

29. The method of claim 1, wherein the symmetrical microvortices are generated at a Reynolds number of between about 30 to 150.

30. The method of claim 29, wherein the Reynolds number is from about 30 to about 100.

31. The method of claim 1, wherein the width of the central fluid inlet channel and the two outer fluid inlet channels is between about 10 and about 500 microns.

32. The method of claim 1, wherein the height of the central fluid inlet channel and the two outer fluid inlet channels is between about 20 and about 1000 microns.

33. The method of claim 1, wherein the length of the central fluid inlet channel and the two outer fluid inlet channels is about 10 mm to about 20 mm.

34. The method of claim 1, wherein the width of the mixing channel is greater than 100 microns.

35. The method of claim 1, wherein the length of the mixing channel is greater than about 10 millimeters.

36. The method of claim 1, wherein the population of the nanoparticles have a polydispersity of about 0.1 or less.

37. The method of claim 1, wherein the nanoparticles are lipid nanoparticles.

\* \* \* \* \*